United States Patent
Antoniotti et al.

(10) Patent No.: US 10,323,210 B2
(45) Date of Patent: Jun. 18, 2019

(54) BIOTECHNOLOGICAL MANUFACTURE OF VETIVERYL ESTERS

(71) Applicants: CENTRE NATIONAL DE LA RECHERCHE SCIENTIFIQUE—CNRS, Paris (FR); UNIVERSITÉ DE NICE-SOPHIA ANTIPOLIS, Nice (FR)

(72) Inventors: Sylvain Antoniotti, Villeneuve-Loubet (FR); Jean-Jacques Filippi, Nice (FR); Irene Notar Francesco, Mougins (FR); Jade Ramilijaona, Monteux (FR)

(73) Assignees: CENTRE NATIONAL DE LA RECHERCHE SCIENTIFIQUE—CNRS, Paris (FR); UNIVERSITÉ DE NICE-SOPHIA ANTIPOLIS, Nice (FR)

( * ) Notice: Subject to any disclaimer, the term of this patent is extended or adjusted under 35 U.S.C. 154(b) by 0 days.

(21) Appl. No.: 15/578,069

(22) PCT Filed: May 30, 2016

(86) PCT No.: PCT/EP2016/062160
§ 371 (c)(1),
(2) Date: Nov. 29, 2017

(87) PCT Pub. No.: WO2016/193208
PCT Pub. Date: Dec. 8, 2016

(65) Prior Publication Data
US 2018/0148666 A1 May 31, 2018

(30) Foreign Application Priority Data
May 29, 2015 (EP) ..................................... 15305835

(51) Int. Cl.
*C11B 9/00* (2006.01)
*C12P 7/62* (2006.01)

(52) U.S. Cl.
CPC .......... *C11B 9/0053* (2013.01); *C11B 9/0003* (2013.01); *C11B 9/0042* (2013.01); *C11B 9/0057* (2013.01); *C12P 7/62* (2013.01)

(58) Field of Classification Search
CPC ........................... C11B 9/0003; C11B 9/0053
See application file for complete search history.

(56) References Cited

PUBLICATIONS

International Search Report of the International Searching Authority issued in PCT/EP2016/062160 dated Aug. 23, 2016 (2 pages).

(Continued)

*Primary Examiner* — Arrie L Reuther
(74) *Attorney, Agent, or Firm* — Osha Liang LLP

(57) ABSTRACT

The invention relates to a vetiveryl ester comprising at least 0.5 weight percent of secondary alcohol compounds with respect to the total weight of the vetiveryl ester and to a process for the preparation a vetiveryl ester, the process comprising: providing a vetiver oil, at least one enzyme preparation and at least one acylating compound; and allowing sufficient time for the enzyme preparation to esterify the alcohol compounds of the vetiver oil with the acylating compound. The invention also relates to a vetiveryl ester obtainable by the above process, a fragrance composition comprising an above-mentioned vetiveryl ester and the use of an above-mentioned vetiveryl ester for the preparation of a perfumed product.

16 Claims, 7 Drawing Sheets

(56) References Cited

PUBLICATIONS

Written Opinion of the International Searching Authority issued in PCT/EP2016/062160 dated Aug. 23, 2016 (7 pages).
Belhassen, E. et al.; "Unravelling the Scent of Vetiver: Identification of Character-Impact Compounds"; Chemistry & Biodiversity, vol. 11, No. 11, Nov. 1, 2014, pp. 1821-1842 (22 pages).
Antoniotti, S.; "Tuning of Essential Oil Properties by Enzymatic Treatment: Towards Sustainable Processes for the Generation of New Frangrance Ingredients"; Molecules, vol. 19, No. 7, Jul. 1, 2014, pp. 9203-9214 (12 pages).

BIOTECHNOLOGICAL MANUFACTURE OF VETIVERYL ESTERS

TECHNICAL FIELD

The present disclosure relates to vetiveryl esters, a process for the preparation of vetiveryl esters, a fragrance composition comprising vetiveryl esters and the use of the above vetiveryl esters, vetiveryl esters prepared by the above process, or the above fragrance composition for the preparation of a perfumed product.

BACKGROUND

Vetiver oil is a composition extracted from *Vetiveria zizanioides* (Gramineae), also called *Chrysopogon zizanioides*. Extracts and modified extracts such as tinctures, concretes, absolutes, essential oils, oleoresins, terpenes, terpene-free fractions, distillates, residues, etc., obtained from *Vetiveria zizanioides* (Gramineae) are also known (CAS: 84238-29-9; EINECS: 282-490-8). Vetiver oil is also used as a substrate to provide fragrance constituents and compositions such as *vetiveria zizanioides* extracts (CAS: 84082-84-8; EINECS: 282-031-1), vetiveryl acetate (CAS: 62563-80-8; EINECS: 204-225-7, 263-597-9), vetiverol (CAS: 68129-81-7; EINECS: 268-578-9), vetiverol acetate (CAS: 62563-80-8; EINECS: 263-597-9) and *vetiveria Zizanioides* (CAS: 8016-96-4; RTECS: YY3180000).

Known vetiveryl esters such as vetiveryl acetate, as used in perfumery and fragrance compositions, are a mixture of products prepared by a chemical reaction between compounds of the vetiver oil with anhydrides, such as the acetylation of alcohol compounds of the vetiver oil with acetic anhydride. Specifically, vetiveryl acetate is generally prepared by industrial acetylation of vetiver oil or vetiverol using acetic anhydride either with or without a catalyst at temperatures up to 120° C., with orthophosphoric acid at room temperature, or with sodium acetate in refluxing toluene followed by distillation, as described by the opinion SCCP/0984/06 of the scientific committee on consumer products of the European commission for health and consumer protection.

Generally, the esterification reaction of vetiver oil is performed in order to modify the olfactory properties of the oil. However, there exists a continuing need to provide vetiveryl esters compositions having more appreciable and subtle set of odor notes. In addition, the stability of known vetiveryl esters is often quite poor. Also, known processes of preparation of known vetiveryl esters need to be improved in regards of sustainability and environment impact. Negative impacts in these processes could be the use of an organic solvent from petrochemistry, the use of additives used in overstoichiometric, stoichiometric or substoichiometric amounts, resulting in many instances in the production of large amounts of waste. For example, acetylation by acetic anhydride is typically performed with this reagent in excess, resulting in the formation of one equivalent or more of acetic acid per ester formed. The energy consumption of these processes is generally high, either to reach the desired reaction temperature or during distillation steps during the work-up. Common processes being based on the use of synthetic carboxylic anhydrides as acylating agents, and common chemicals as additives, the resulting vetiveryl esters are classified as synthetic products.

Accordingly, there exists a continuing need to provide vetiveryl esters with original olfactory properties produced by sustainable processes.

SUMMARY

An object of the present disclosure is to provide a superior quality class of vetiveryl esters having an enhanced, equilibrated and pleasant set of odor notes. Another object of the present disclosure is to provide more stable vetiveryl esters. A further object of the present disclosure is to provide natural vetiveryl esters. A further object of the present disclosure is to provide a less energy intensive, more reproducible and more environmentally friendly process for the preparation of vetiveryl esters.

According to a first aspect, the above-mentioned objects, as well as further advantages, are achieved by a vetiveryl ester comprising at least 0.5 weight percent of secondary alcohol compounds with respect to the total weight of the vetiveryl ester.

According to a second aspect, one or more of the above-mentioned objects are achieved by a process for the preparation of a vetiveryl ester such as the vetiveryl ester according to the first aspect, the process comprising: providing a vetiver oil, at least one enzyme preparation and at least one acylating compound; and allowing sufficient time for the enzyme preparation to esterify the alcohol compounds of the vetiver oil with the acylating compound.

According to a third aspect, one or more of the above-mentioned objects are achieved by a vetiveryl ester obtainable by the process according to the second aspect.

According to the invention, the vetiveryl esters of the invention are obtained from a vetiver oil and may comprise substantially no primary alcohol compounds, as substantially all primary alcohol compounds present in the vetiver oil are esterified (e.g. no more than 5 weight percent of primary alcohol compounds with respect to the total weight of the vetiveryl ester); substantially the same amount of secondary alcohol compounds as the amount of secondary alcohol compounds present in the vetiver oil (e.g. ±5 absolute deviation in weight percent of secondary alcohol compounds present in the vetiveryl ester with respect to the amount of secondary alcohol compounds present in the vetiver oil); and substantially the same amount of tertiary alcohol compounds as the amount of tertiary alcohol compounds present in the vetiver oil (e.g. ±5 absolute deviation in weight percent of tertiary alcohol compounds present in the vetiveryl with respect to the amount of tertiary alcohol compounds present in the vetiver oil).

According to a fourth aspect, one or more of the above-mentioned objects are achieved by a fragrance composition comprising the vetiveryl ester according to the first aspect, the vetiveryl ester prepared by the process according to the second aspect or the vetiveryl ester according to the third aspect.

According to a fifth aspect, one or more of the above-mentioned objects are achieved by a use of the vetiveryl ester according to the first aspect, the vetiveryl ester prepared by the process according to the second aspect, the vetiveryl ester according to the third aspect or the fragrance composition according to the fourth aspect for the preparation of a perfumed product.

Embodiments of the present disclosure according to the above aspects are defined in the appended claims.

Other aspects and advantages of the present disclosure will be apparent from the following Figures, description and appended claims.

BRIEF DESCRIPTION OF DRAWINGS

The present disclosure will be better understood and other advantages and embodiments will become clear on reading the description that follows, given purely by way of indication and in no way limiting, and by referring to the appended Figures in which:

FIG. 3b shows a chromatogram of the saponification products of the isolated ester fraction according to FIG. 3a.

DETAILED DESCRIPTION OF EMBODIMENTS

Figure 1A:
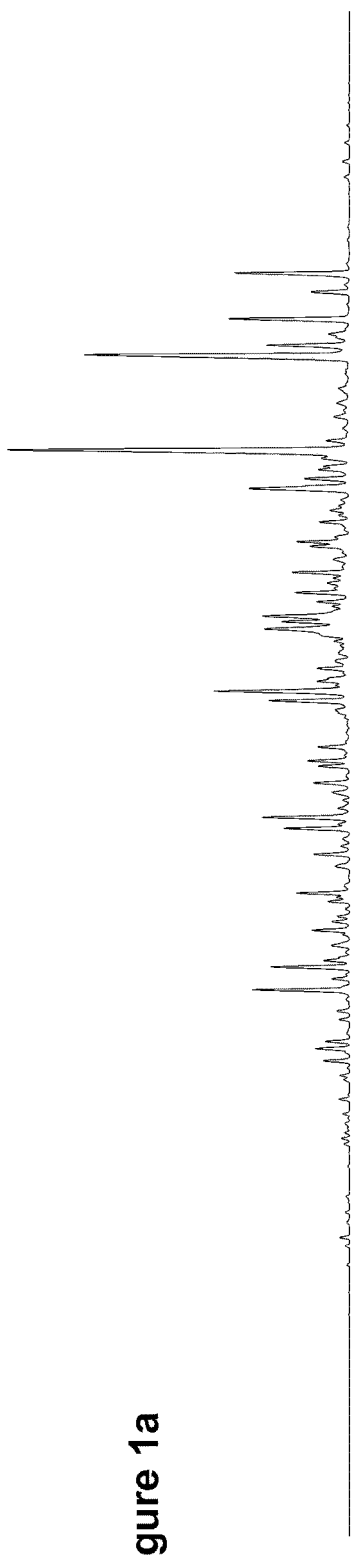
FIG. 1a shows a chromatogram of Haitian vetiver essential oil.

Embodiments of the present disclosure will now be described in detail with reference to the accompanying Figures. In the following detailed description of embodiments of the present disclosure, numerous specific details are set forth in order to provide a more thorough understanding of the present disclosure. However, it will be apparent to one of ordinary skill in the art that the present disclosure may be practiced without these specific details. In other instances, well-known features have not been described in detail to avoid unnecessarily complicating the description.

Herein, the words "comprise/comprising" are synonymous with (means the same thing as) "include/including," "contain/containing", are inclusive or open-ended and do not exclude additional, non-recited elements. Further, herein the term "about" and "substantially" are synonymous with (means the same thing as) a 20 percent lower and/or higher margin of the respective value. The term "weight percent" apply to the weight of a given compound divided by the weight of the reference substance, in most instances unless specified, the vetiveryl ester. The term "weight percent" also apply by extension to the percentage of a given compound in the composition of the whole reference substance, in most instances, the vetiveryl ester, determined with a gas chromatograph equipped with flame ionization detector (FID) or any type of quantitative detector, existing or to be developed in the future, presenting similar or superior performance compared with the FID. For comparison purpose, "weight percent" also apply to the percentage of a given compound in the composition of the whole reference substance, in most instances, the vetiveryl ester, determined with a gas chromatograph equipped with mass spectrometer (GC-MS), such as determined with a two-dimensional comprehensive gas chromatograph equipped with mass spectrometer (GC×GC-MS), as in Table 1.

In the following, it is meant by "vetiveryl ester" a composition produced from esterification of a vetiver oil. In the following, it is meant by "natural compound" a compound produced by a non-denaturing process from chemical substances extracted from living organisms or created by the living. In the following, it is meant by "acylating compound" a compound of formula RCOX, wherein R is a hydrogen atom or a linear, cyclic or branched, saturated or unsaturated, C1-C20 organic substituent, and wherein X is a leaving group. In one or more embodiment, the C1-C20 organic substituent is selected from the group comprising C1-C20 alkyl, C2-C20 alkenyl, a C2-C20 alkynyl, C1-C20 alkoxy, C1-C20 alkylthio, C1-C20 alkylamino, C1-C20 alkylamido, C2-C20 heteroalkyl, C1-C20 haloalkyl, C6-C20 aryl, C4-C20 heteroaryl, C7-C20 alkylaryl, C7-C20 arylalkyl, C8-C20 arylalkenyl, C8-C20 arylalkynyl, C6-C20 haloaryl, C2-C20 alkylketone, C2-C20 alkylthione and C2-C20 alkylcarbonate. In one or more embodiments, the C1-C20 organic substituent is a C1-C20 alkyl. In one or more embodiments, the C1-C20 organic substituent is a C1-C4 alkyl such as a methyl or an ethyl group. In one or more embodiment, the leaving group is selected from the group comprising alkoxides (OR'), hydroxide, carboxylates (OCOR'), alkoxyalkyls, sulfonates, perfluoroalkylsulfonates ($OSO_2R'F$), tosylates, mesylates, iodide, bromide, chloride, fluoride, nitrate, phosphate, thiolates ($SR_2^+$), amines ($NR'_2$, $NR'_3^+$), ammonia and dinitrogen (diazo), wherein R' are identical or different and are each a linear, cyclic or branched, saturated or unsaturated, C1-C20 organic substituent as R is defined above, or a hydrogen atom. In one or more embodiments, the leaving group is selected from the group comprising alkoxides, hydroxide and carboxylates. In one or more embodiments, the leaving group is an alkoxide. In one or more embodiments, the leaving group is an ethylate ($CH_3CH_2O$).

The inventors developed a new process for obtaining new vetiveryl esters by enzymatic esterification. The vetiveryl esters of the invention comprise substantially no primary alcohol compounds, as substantially all primary alcohol compounds present in the vetiver oil are esterified (e.g. no more than 5 weight percent of primary alcohol compounds with respect to the total weight of the vetiveryl ester); and substantially the same amount of secondary and tertiary alcohol compounds as the amount of secondary and tertiary alcohol compounds present in the vetiver oil, respectively (e.g. ±10 or ±5 absolute deviation in weight percent of secondary alcohol compounds present in the vetiveryl ester with respect to the amount of secondary alcohol compounds present in the vetiver oil; and ±10 or ±5 absolute deviation in weight percent of tertiary alcohol compounds present in the vetiveryl with respect to the amount of tertiary alcohol compounds present in the vetiver oil).

The present disclosure provides, according to a first aspect, a vetiveryl ester comprising at least 0.5 weight percent of secondary alcohol compounds with respect to the total weight of the vetiveryl ester. This composition may be used to prepare perfumes and cosmetic products in view of the increasing commercial importance of this market, for example. Furthermore, these vetiveryl esters were found to have enhanced, equilibrated, long lasting, stable and pleasant set of odor notes as follow: grapefruit-like, sandalwood-like, cedarwood-like, smoky and powdery.

In one or more embodiments, the vetiveryl ester comprises from about 0.5 weight percent to about 15 weight percent of the secondary alcohol compounds with respect to the total weight of the vetiveryl ester. In one or more embodiments, the vetiveryl ester comprises from about 1 weight percent to about 10 weight percent of the secondary alcohol compounds with respect to the total weight of the vetiveryl ester.

In one or more embodiments, the secondary alcohol compounds comprise at least one alcohol selected from the following list: 12-nor-zizaen-2β-ol, junenol, ziza-6(13)-en-3α-ol, khusian-2-ol, nootkatol, β-vetivol, β-isonootkatol and isonootkatol. In one or more embodiments, the secondary alcohol compounds comprise at least one alcohol selected from the following list: junenol, isocedranol, ziza-6(13)-en-3α-ol, khusian-2-ol, nootkatol, β-isonootkatol, β-vetivol, 12-nor-zizaen-2β-ol, 12-nor-zizaen-2α-ol, and α-isonootkatol. In one or more embodiments, the secondary alcohol compounds comprise at least one alcohol selected from the following list: α-isonootkatol (1), β-vetivol (2), ziza-6(13)-en-3α-ol (3), ziza-6(13)-en-3β-ol (4) and junenol (5), as shown below. In one or more embodiments, the secondary alcohol compounds comprise at least one alcohol selected from the following list: α-isonootkatol (1), β-vetivol (2), ziza-6(13)-en-3α-ol (3) and junenol (5).

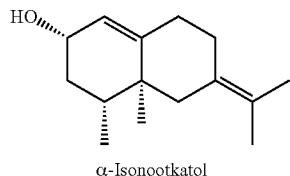

α-Isonootkatol

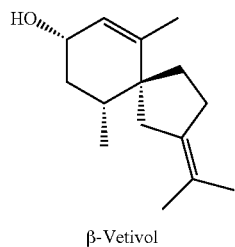

β-Vetivol

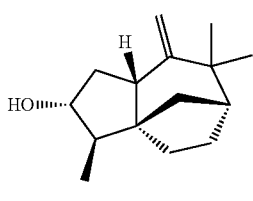

Ziza-6(13)-en-3α-ol

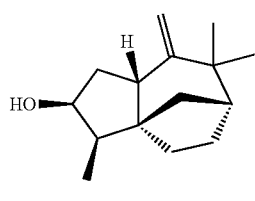

Ziza-6(13)-en-3β-ol

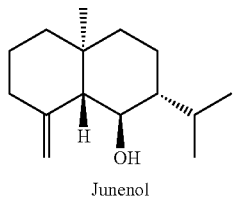

Junenol

In one or more embodiments, the vetiveryl ester comprises from about 0.5 weight percent to about 7.5 weight percent of α-isonootkatol (1) with respect to the total weight of the vetiveryl ester. In one or more embodiments, the vetiveryl ester comprises from about 0.5 weight percent to about 4.5 weight percent of β-vetivol (2) with respect to the total weight of the vetiveryl ester. In one or more embodiments, the vetiveryl ester comprises from about 0.2 weight percent to about 3.3 weight percent of ziza-6(13)-en-3α-ol (3) with respect to the total weight of the vetiveryl ester. In one or more embodiments, the vetiveryl ester comprises from about 0.2 weight percent to about 2.4 weight percent of ziza-6(13)-en-3α-ol (3) with respect to the total weight of the vetiveryl ester. In one or more embodiments, the vetiveryl ester comprises from about 0.1 weight percent to about 5 weight percent of ziza-6(13)-en-3β-ol (4) with respect to the total weight of the vetiveryl ester. In one or more embodiments, the vetiveryl ester comprises from about 0.0 weight percent to about 3.0 weight percent of junenol (5) with respect to the total weight of the vetiveryl ester. In one or more embodiments, the vetiveryl ester comprises from about 0.1 weight percent to about 3.1 weight percent of junenol (5) with respect to the total weight of the vetiveryl ester.

In one or more embodiments, the vetiveryl ester comprises no more than 5 weight percent of primary alcohol compounds with respect to the total weight of the vetiveryl ester. In one or more embodiments, the vetiveryl ester comprises from about 1 weight percent to about 5 weight percent of primary alcohol compounds with respect to the total weight of the vetiveryl ester, for example from about 1.25 weight percent to about 2.5 weight percent, for example from about 1.5 weight percent to about 2.5 weight percent.

In one or more embodiments, the primary alcohol compounds comprise at least one alcohol selected from the following list: cyclocopacamphanol A, cyclocopacamphanol B, vetiselinenol, khusimol, valencen-12-ol, (I)-isovalencenol and spirovetivadien-12-ol. In one or more embodiments, the primary alcohol compounds comprise at least one alcohol selected from the following list: cyclocopacamphanol A, cyclocopacamphanol B, vetiselinenol, khusimol, valencen-12-ol, (E/Z)-isovalencenol and spirovetivadien-12-ol. In one or more embodiments, the primary alcohol compounds comprise at least one alcohol selected from the following list: khusimol (6), (E/Z)-isovalencenol, vetiselinenol (8), spirovetiva-3,7(11)-dien-12-ol (9), cyclocopacamphanol A (10) and cyclocopacamphanol B (11), as shown below. In one or more embodiments, the primary alcohol compounds comprise at least one alcohol selected from the following list: khusimol (6), (E)-isovalencenol (7), vetiselinenol (8), spirovetiva-3,7(11)-dien-12-ol (9), cyclocopacamphanol A (10) and cyclocopacamphanol B (11), as shown below.

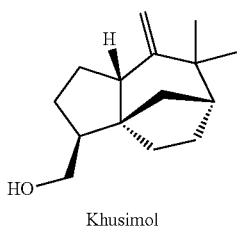

Khusimol

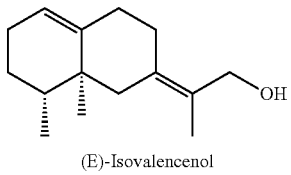

(E)-Isovalencenol

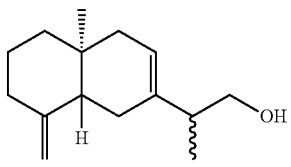

Vetiselinenol

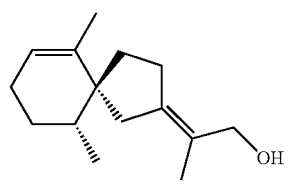

Spirovetiva-3,7(11)-dien-12-ol

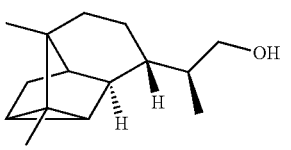

Cyclocopacamphanol A

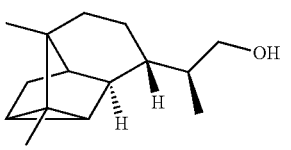

Cyclocopacamphanol B

In one or more embodiments, the vetiveryl ester comprises from about 0 weight percent to about 1 weight percent of khusimol (1) with respect to the total weight of the vetiveryl ester. In one or more embodiments, the vetiveryl ester comprises from about 0 weight percent to about 2 weight percent of (E/Z)-isovalencenol (7) with respect to the total weight of the vetiveryl ester. In one or more embodiments, the vetiveryl ester comprises from about 0 weight percent to about 1 weight percent of (E)-isovalencenol (7) with respect to the total weight of the vetiveryl ester. In one or more embodiments, the vetiveryl ester comprises from about 0 weight percent to about 1 weight percent of vetiselinenol (8) with respect to the total weight of the vetiveryl ester. In one or more embodiments, the vetiveryl ester comprises from about 0 weight percent to about 1 weight percent of spirovetiva-3,7(11)-dien-12-ol (9) with respect to the total weight of the vetiveryl ester. In one or more embodiments, the vetiveryl ester comprises from about 0 weight percent to about 1 weight percent of cyclocopacamphanol A (10) with respect to the total weight of the vetiveryl ester. In one or more embodiments, the vetiveryl ester comprises from about 0 weight percent to about 1 weight percent of cyclocopacamphanol B (11) with respect to the total weight of the vetiveryl ester.

In one or more embodiments, the vetiveryl ester comprises at least 2.5 weight percent of tertiary alcohol compounds with respect to the total weight of the vetiveryl ester. In one or more embodiments, the vetiveryl ester comprises from about 2.5 weight percent to about 25 weight percent of the tertiary alcohol compounds with respect to the total weight of the vetiveryl ester. In one or more embodiments, the vetiveryl ester comprises at least 10 weight percent of tertiary alcohol compounds with respect to the total weight of the vetiveryl ester. In one or more embodiments, the vetiveryl ester comprises from about 10 weight percent to about 20 weight percent of the tertiary alcohol compounds with respect to the total weight of the vetiveryl ester.

In one or more embodiments, the tertiary alcohol compounds comprise at least one alcohol selected from the following list: elemol, cis-eudesm-6-en-11-ol, cis-eudesm-6-en-4-ol A, cis-eudesm-6-en-4-ol B, 10-epi-γ-eudesmol, β-eudesmol, 1-epi-cubenol, hinesol, α-cadinol epimer, α-cadinol, valerianol, α-eudesmol, intermedeol and juniper camphor. In one or more embodiments, the tertiary alcohol compounds comprise at least one alcohol selected from the following list: β-elemol, cis-eudesm-6-en-11-ol, cis-eudesm-6-en-4-ol A, cis-eudesm-6-en-4-ol B, 10-epi-γ-eudesmol, β-eudesmol, 1-epi-cubenol, α-cadinol epimer, α-cadinol, valerianol, α-eudesmol, and juniper camphor. In one or more embodiments, the tertiary alcohol compounds comprise at least one alcohol selected from the following list: cis-eudesm-6-en-11-ol (12), 10-epi-γ-eudesmol (13), cis-eudesm-6-en-4-ol A & B (14), juniper camphor (15), α-eudesmol (16) and α-cadinol (17), as shown below.

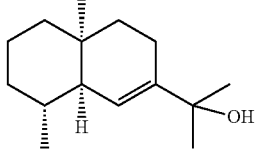

cis-Eudesm-6-en-11-ol

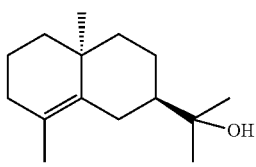

10-epi-γ-Eudesmol

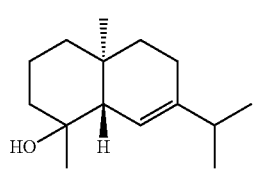

cis-Eudesm-6-en-4-ol A & B

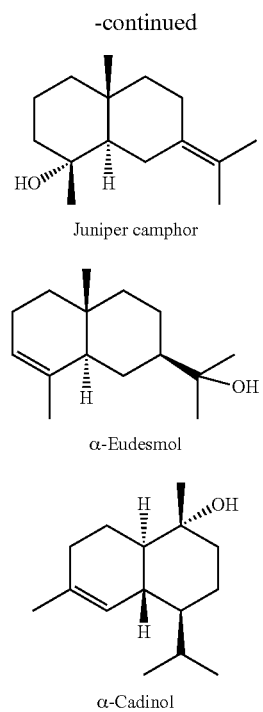

Juniper camphor

α-Eudesmol

α-Cadinol

In one or more embodiments, the vetiveryl ester comprises from about 0.5 weight percent to about 3 weight percent of cis-eudesm-6-en-11-ol (12) with respect to the total weight of the vetiveryl ester. In one or more embodiments, the vetiveryl ester comprises from about 0.0 weight percent to about 2.5 weight percent of 10-epi-γ-eudesmol (13) with respect to the total weight of the vetiveryl ester. In one or more embodiments, the vetiveryl ester comprises from about 0.25 weight percent to about 2.5 weight percent of 10-epi-γ-eudesmol (13) with respect to the total weight of the vetiveryl ester. In one or more embodiments, the vetiveryl ester comprises from about 0.5 weight percent to about 9 weight percent of cis-eudesm-6-en-4-ol A & B (14) with respect to the total weight of the vetiveryl ester. In one or more embodiments, the vetiveryl ester comprises from about 0.5 weight percent to about 4 weight percent of cis-eudesm-6-en-4-ol A & B (14) with respect to the total weight of the vetiveryl ester. In one or more embodiments, the vetiveryl ester comprises from about 0.25 weight percent to about 3 weight percent of juniper camphor (15) with respect to the total weight of the vetiveryl ester. In one or more embodiments, the vetiveryl ester comprises from about 0 weight percent to about 1 weight percent of α-eudesmol (16) with respect to the total weight of the vetiveryl ester. In one or more embodiments, the vetiveryl ester comprises from about 0.75 weight percent to about 4.5 weight percent of α-cadinol (17) with respect to the total weight of the vetiveryl ester.

In one or more embodiments, the vetiveryl ester comprises from about 1 to about 50 weight percent of ester compounds with respect to the total weight of the vetiveryl ester. In one or more embodiments, the vetiveryl ester comprises from about 25 to about 45 weight percent of ester compounds with respect to the total weight of the vetiveryl ester. In one or more embodiments, the vetiveryl ester comprises from about 35 to about 45 weight percent of ester compounds with respect to the total weight of the vetiveryl ester.

In one or more embodiments, the ester compounds comprise at least one ester selected from the following list: 12-norzizaen-2β-yl acetate, 12-norzizaen-2α-yl acetate, eudesm-6-en-4-yl acetate, eudesma-4(15),6-dien-3β-yl acetate, cyclocopacamphanyl acetate A, cyclocopacamphanyl acetate B, khusian-2-yl acetate, zizaen-3α-yl acetate, zizaen-3β-yl acetate, vetiselinenyl acetate, khusimyl acetate, spirovetivadien-2-yl acetate, isonootkatyl acetate, spirovetivadien-12-yl acetate, (E)-isovalencenyl acetate and (Z)-isovalencenyl acetate. In one or more embodiments, the ester compounds comprise at least one ester selected from the following list: 12-norzizaen-2β-yl acetate, 12-norzizaen-2α-yl acetate, cyclocopacamphanyl acetate A, cyclocopacamphanyl acetate B, khusian-2-yl acetate, zizaen-3α-yl acetate, zizaen-3β-yl acetate, vetiselinenyl acetate, khusimyl acetate, spirovetivadien-2-yl acetate, isonootkatyl acetate, spirovetivadien-12-yl acetate, (E)-isovalencenyl acetate and (Z)-isovalencenyl acetate. In one or more embodiments, the ester compounds comprise at least one ester selected from the following list: cyclocopacamphanyl acetate A, cyclocopacamphanyl acetate B, vetiselinenyl acetate, khusimyl acetate, spirovetivadien-12-yl acetate, (E)-isovalencenyl acetate and (Z)-isovalencenyl acetate. In one or more embodiments, the vetiveryl ester comprises from about 25 weight percent to about 40 weight percent of cyclocopacamphanyl acetate A, cyclocopacamphanyl acetate B, vetiselinenyl acetate, khusimyl acetate, spirovetivadien-12-yl acetate, (E)-isovalencenyl acetate and (Z)-isovalencenyl acetate with respect to the total weight of the vetiveryl ester. In one or more embodiments, the vetiveryl ester comprises from about 35 weight percent to about 40 weight percent of cyclocopacamphanyl acetate A, cyclocopacamphanyl acetate B, vetiselinenyl acetate, khusimyl acetate, spirovetivadien-12-yl acetate, (E)-isovalencenyl acetate and (Z)-isovalencenyl acetate with respect to the total weight of the vetiveryl ester. In these embodiments, one or more ester compounds may comprise an acyl group (RCO) in place of the acetate. In these embodiments, one or more ester compounds may comprise a formate and/or a propionate in place of the acetate.

The development of an atom economical and biotechnological process to produce vetiveryl esters according to the present disclosure at affordable costs is also provided herein. According to a second aspect, the present disclosure provides a process for the preparation of vetiveryl esters according to the first aspect, the process comprising: providing a vetiver oil, at least one enzyme preparation and at least one acylating compound; and allowing sufficient time for the enzyme preparation to esterify the acylating compound with alcohol compounds of the vetiver oil. Indeed, in regards of the environmental impact of chemical processes such as the industrial acetylation of vetiver oil, the above-mentioned sustainable enzymatic process based on the use of natural renewable resources was found to provide vetiveryl esters according to the first aspect, as synthesized. As described above, the process of the invention allows to obtain a vetiveryl ester comprising no primary alcohol compounds, as substantially all primary alcohol compounds present in the vetiver oil are esterified (e.g. no more than 5 weight percent of primary alcohol compounds with respect to the total weight of the vetiveryl ester); and substantially the same amount of secondary and tertiary alcohol compounds as the amount of secondary and tertiary alcohol compounds present in the vetiver oil, respectively (e.g. ±10 or ±5 absolute deviation in weight percent of secondary alcohol compounds present in the vetiveryl ester with respect to the amount of secondary alcohol compounds present in the vetiver oil; and ±10 or ±5 absolute deviation in weight percent of tertiary alcohol compounds present in the vetiveryl with respect to the amount of tertiary alcohol compounds present in the vetiver oil).

In addition, although the low productivity and the overall cost of enzymatic processes and the low thermal and chemical stability of enzymes are notorious drawback of biocatalysis for industrial applications, the process according to one or more embodiments of the present disclosure provides vetiveryl esters in high yield and productivity and with low energy consumption. In fact, dealing with natural extracts transformation, enzymes were rarely used before, because of the high complexity of the chemical composition of natural extracts, and the subsequent risk of inhibition of the enzyme and non-specific reactions likely to occur. Indeed, scarce examples of enzymatic modifications of essential oils were reported in the scientific literature. For example, inventors of the present disclosure described in *Chem. Biodiv.*, 2013, 10 (12), 2291-2301, that a high enzyme loading for the free lipase-catalyzed acetylation of palmarosa essential oil was necessary due to a saturation phenomenon. In most reported cases, the enzymatic treatment occur before the production of the natural extract, the role of the enzyme being to pre-process the raw material by a hydrolytic activity (cellulase, glycosidase) as described by inventors of the present disclosure in *Molecules* 2014, 19 (7), 9203-9214.

In one or more embodiments, the esterification is performed in presence of a drying agent. In one or more embodiments, the drying agent is selected from the group comprising calcium hydride, calcium chloride, calcium sulfate, magnesium sulfate, sodium carbonate, sodium sulfate, phosphorus pentoxide and microporous aluminosilicate. In one or more embodiments, the drying agent comprises microporous aluminosilicate such as molecular sieves. In one or more embodiments, the molecular sieves have a pore size ranging from 1 Å to 5 Å. In one or more embodiments, the molecular sieves have a pore size of about 3 Å. Indeed, performing the process in the presence of a drying agent such as a microporous aluminosilicate was found to be beneficial as a low level of residual water may be maintained in the reaction medium, thereby avoiding the undesirable production of carboxylic acid (e.g. acetic acid), which may cause of a loss of olfactory quality of the product during the process or during the aging of the vetiveryl ester.

In one or more embodiments, the enzyme preparation comprises at least one esterase. In one or more embodiments, the esterase is a lipase. The use of a lipase allow the process to be performed safely as lipases are generally recognized as safe (GRAS). Indeed, lipases are currently used in dairy products treatments in industry. In one or more embodiment, the esterase is selected from the group comprising pig liver esterase, *Bacillus subtilis* esterase, *Bacillus stearothermophilus* esterase, *Rhizopus oryzae* esterase, *Candida lipolytica* esterase, *Mucor miehei* esterase, *Saccharomyces cerevisiae* esterase, horse liver esterase, hog liver esterase, *Pseudomonas fluorescens* esterase, *Candida rugosa* lipase (formerly *Candida cylindracea* lipase), *Pseudomonas cepacia* lipase, *Aspergillus* sp. lipase, *Mucor miehei* lipase, *Pseudomonas fluorescens* lipase, *Rhizopus arrhizus* lipase, *Rhizopus niveus* lipase, lipase from porcine pancreas, *Aspergillus oryzae* lipase, *Mucor javanicus* lipase, *Penicillium roqueforti* lipase, lipase from wheat germ, *Rhizopus oryzae* lipase, human lipase such as pancreatic lipase and *Candida antartica* lipase, either extracted from their natural source and regardless of their purity or heterologously expressed by recombinant organisms such as *Escherichia coli, Aspergillus niger* or any other host. In one or more embodiments, the lipase is *Candida antartica* lipase B.

In one or more embodiments, the enzyme preparation is a supported enzyme preparation. In one or more embodiments, the supported enzyme preparation is a resin supported enzyme preparation. In one or more embodiments, the resin supported enzyme preparation is an organic resin supported enzyme preparation, such as an acrylic resin supported enzyme preparation. In one or more embodiments, the supported enzyme preparation has an activity of at least 1000 U/g. In one or more embodiments, the supported enzyme preparation has an activity of at least 5000 U/g. The use of a supported enzyme allows recycling the biocatalyst as well as performing the process continuously, which is an additional improvement in regards of sustainability as well as environment impact compared to known processes. Moreover, the largely improved thermal and chemical stability of the supported enzyme and the possibility to run the reactions in a food grade solvent instead of water, which is generally the mandatory solvent for enzymatic reactions, allowed a significant increase of the productivity by increasing vetiver oil concentration up to 250 g/L, for example.

In one or more embodiments, the vetiver oil is selected from the group comprising tinctures, concretes, absolutes, essential oils, oleoresins, terpenes, terpene-free fractions, supercritical $CO_2$ extracts, HFC extracts, distillates and residues extracted from *Vetiveria zizanioides*. In one or more embodiments, the vetiver oil is a vetiver essential oil. In one or more embodiments, the vetiver oil is obtained from the root of vetiver. In one or more embodiments, the vetiver oil is natural vetiver oil. In one or more embodiments, the vetiver oil is a vetiverol fraction oil (i.e., an alcohol fraction of vetiver oil). According to these embodiments, the process may provide vetiverol esters (i.e., an esterified alcohol fraction of vetiver oil).

In one or more embodiments, the acylating compound is selected from the group comprising carboxylic acids, carboxylic acid anhydrides, acyl halides, carboxylic acid esters, carboxylic acid thioesters and carboxylic enol esters. For example, the radical of the acyl group of the acylating compound may be linear, cyclic or branched, saturated or unsaturated. For example, the acylating compound may be derived from C1-C20 carboxylic acids. In one or more embodiments, the acylating compound comprises at least one carboxylic acid ester. In one or more embodiments, the carboxylic acid ester comprises a methyl, an ethyl and/or a propyl formate, acetate (i.e., methyl, ethyl and/or propyl ethanoate) and/or propionate.

In one or more embodiments, the acylating compound is a natural product. For example, the acylating compound is a natural carboxylic acid ester. In one or more embodiments, the acylating compound is natural ethyl acetate. In addition, according to one or more embodiments, the vetiver oil, the acylating compound, the enzyme preparation and an optional solvent are selected from natural compounds. Therefore, in one or more embodiments, the process provides natural vetiveryl esters, the process being performed by way of a biotechnological treatment of natural materials.

In one or more embodiments, the esterification is performed in presence of a solvent. In one or more embodiments, the solvent is selected from the group comprising hydrocarbons (such as pentane, hexane, cyclohexane, heptane, octane in all their isomeric forms, and petroleum ethers), oxygenated solvents (such as dialkyl ethers, cyclic ethers, carboxylic esters, lactones, dialkylcarbonates, cyclic carbonates, alcohols, polyols, glycerol and derivatives, glycols and derivatives, glycol ethers), halogenated solvents (chloroform, dichloromethane, methylchloride, carbon tetrachloride, chlorobenzene, and any hydrocarbon with one or more hydrogen atom(s) replaced by one or more halogen such as fluorine, chlorine, bromine, iodine), nitrogenated solvents (pyridine, amines, pyrolidine, dimethylformamide, nitromethane, acetonitrile), sulfurated solvants (dimethylsulfoxide, sulfolane, carbon disulfide), supercritical fluids ($CO_2$, $CH_4$, water, any fluid beyond its critical points), ionic liquids (liquid at the reaction temperature including room temperature and composed of an organic cation such as an imidazolium or a pyridinium and an anion such as bromide, tetrafluoroborate, hexafluorophosphate, bistrifluorosulfonylimidure, trifluoromethanesulfonate), and water. In one or more embodiments, the solvent comprises ethyl acetate. In one or more embodiments, the solvent comprises natural ethyl acetate. In addition, in one or more embodiments, the acylating compound acts as a solvent. For example, the acylating compound may act as the unique solvent.

In one or more embodiments, the enzyme preparation is allowed to react with the acylating compound and vetiver oil or the alcohol compounds of the vetiver oil for a duration of at least 1 hour. In one or more embodiments, the enzyme preparation is allowed to react with the acylating compound and vetiver oil or the alcohol compounds of the vetiver oil for a duration of at least 1 hour to about 7 days, for example from about 3 hours to about 7 hours such as for a duration of about 5 hours.

In one or more embodiments, the enzyme preparation is allowed to react with the acylating compound and vetiver oil or the alcohol compounds of the vetiver oil at a temperature ranging from about −20° C. to about 80° C. In one or more embodiments, the enzyme preparation is allowed to react with the acylating compound and vetiver oil or the alcohol compounds of the vetiver oil at a temperature ranging from about 10° C. to about 40° C. such as at room temperature.

Examples

Exemplary vetiveryl esters according to one or more embodiments of the present disclosure as well as an exemplary process for producing the same are described therein.

Vetiveryl Ester:

Tables 1a-h show the chemical composition of a Haitian vetiver essential oil, a commercial vetiveryl acetate, a vetiveryl acetate obtained by a chemical process and a vetiveryl ester according to one or more embodiments of the present disclosure. As shown in the gas chromatograph results of Tables 1a-e, the chemical composition of a vetiveryl acetate according to one or more embodiments of the present disclosure is different from the chemical composition of vetiver oils in that the vetiveryl acetate comprises ester compounds. Indeed, the vetiveryl acetate may comprise at least 1 weight percent of ester compounds with respect to the total weight of the vetiveryl acetate. Furthermore, as shown in Tables 1a-h, the chemical composition of the vetiveryl acetate according to one or more embodiments of the present disclosure is different from the chemical composition of commercial vetiveryl acetates and vetiveryl acetates obtained by chemical processes in that the vetiveryl acetate according to one or more embodiments of the present disclosure comprises at least 0.5 weight percent of secondary alcohol compounds with respect to the total weight of the vetiveryl acetate.

For example, Tables 1a-h show that the secondary alcohol ziza-6(13)-en-3α-ol (entry 52) is comprised in amounts of at least 0.1 weight percent with respect to the total weight of the vetiveryl acetate according to one or more embodiments of the present disclosure (see also entries 54, 61 and 68, for example, showing secondary alcohols in at least 0.5 weight percent). Conversely, secondary alcohols such as ziza-6(13)-en-3α-ol (entry 52) are merely comprised in amounts up to 0.1 weight percent with respect to the total weight of commercial vetiveryl acetates and vetiveryl acetates obtained by chemical processes (see also entries 61, 66 and 68, for example). Tables 1a-h also show that esters such as khusimyl acetate (entry 95) is comprised in amounts of at least 9 weight percent with respect to the total weight of the vetiveryl acetate according to one or more embodiments of the present disclosure (see also entries 92, 97, 98 and 100, for example). Conversely, esters such as such as khusimyl acetate (entry 95) are not present in Haitian vetiver oil (see also entries 92, 97, 98 and 100, for example). Last but not least, Tables 1a-h also show that the total amount of primary alcohols is no more than 5 weight percent with respect to the total weight of the vetiveryl acetate according to one or more embodiments of the present disclosure (see entries 47, 49, 72, 78, 84 and 85, for example). Conversely, the total amount of primary alcohols is over 20 weight percent with respect to the total weight of the vetiver oil (see entries 47, 49, 72, 78, 84 and 85, for example).

Figure 1B:
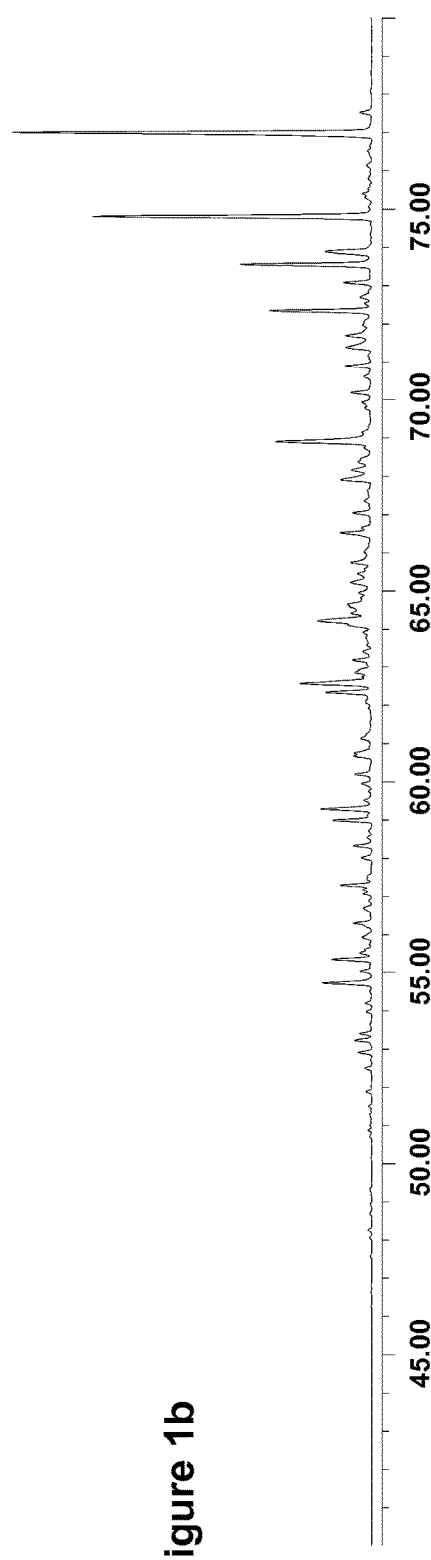
FIG. 1b shows a chromatogram of a vetiveryl ester according to one or more embodiments of the present disclosure.

The above-mentioned differences in chemical composition between the vetiveryl esters according to one or more embodiments of the present disclosure and vetiver oils are also illustrated in FIG. 1a, which shows a chromatogram of Haitian vetiver essential oil comprising a large amount of primary alcohols and no ester compounds, compared to FIG. 1b, which shows a chromatogram of vetiveryl acetate according to one or more embodiments of the present disclosure comprising a very low amount of primary alcohols and a large amount of esterified primary alcohol compounds.

Figures 2A, 2B, 2C:
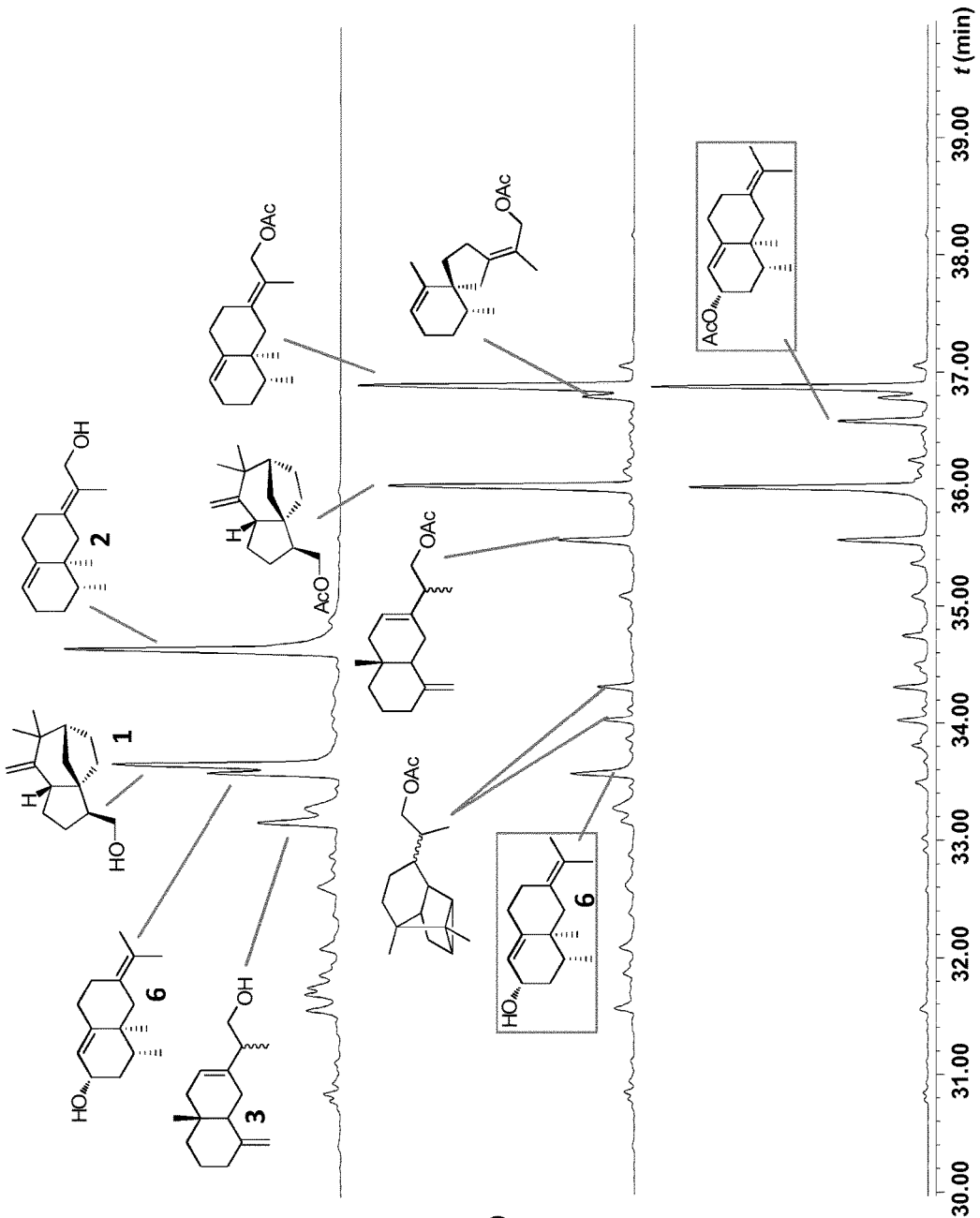
FIG. 2a shows a chromatogram of vetiverol.
FIG. 2b shows a chromatogram of a vetiverol ester according to one or more embodiments of the present disclosure.
FIG. 2c shows a chromatogram of a chemically acetylated vetiverol.

The above-mentioned differences in chemical composition between a vetiveryl ester according to one or more embodiments of the present disclosure, vetiver oils, commercial vetiveryl acetates and vetiveryl acetates obtained by chemical processes, are also illustrated in FIG. 2a, which shows a chromatogram of vetiverol with no ester compounds, and FIG. 2c, which shows a chromatogram of a chemically acetylated vetiverol having a high amount of esterified secondary alcohol compounds and therefore having a low amount of secondary alcohol compounds, compared to FIG. 2b, which shows a chromatogram of vetiverol acetate according to one or more embodiments of the present disclosure having a high amount of esterified primary alcohol compounds, a high amount of secondary alcohol compounds and a very low amount esterified secondary alcohol compounds.

Figure 3A:
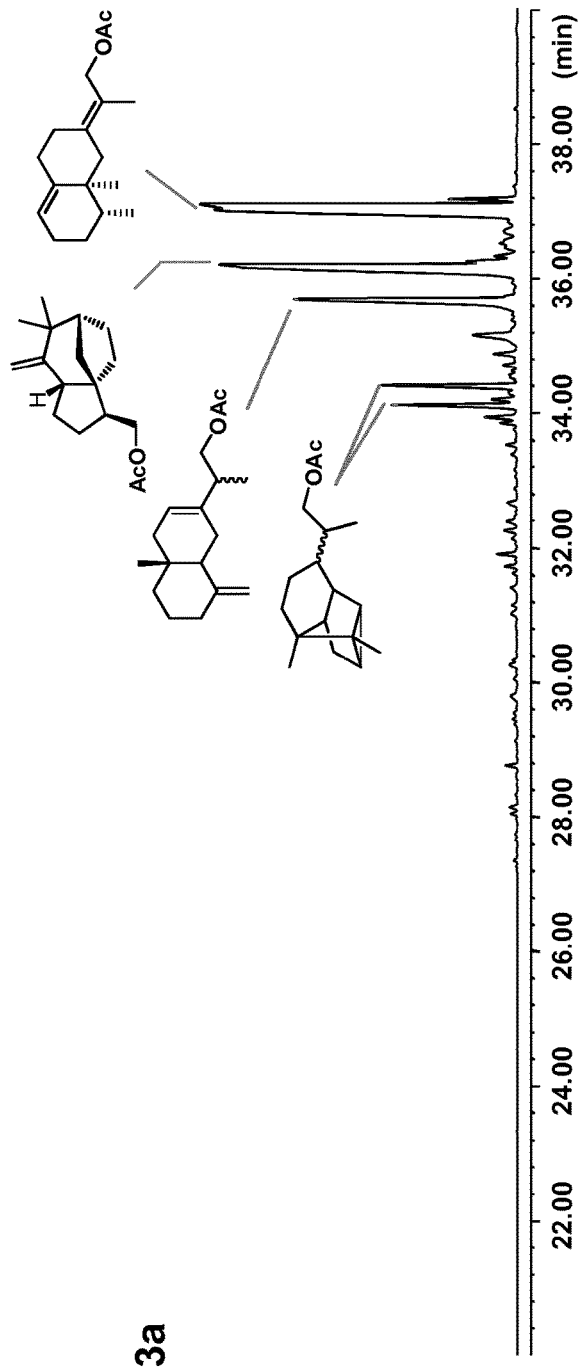
FIG. 3a shows a chromatogram of an ester fraction isolated from a vetiveryl ester according to one or more embodiments of the present disclosure.
Figure 3B:
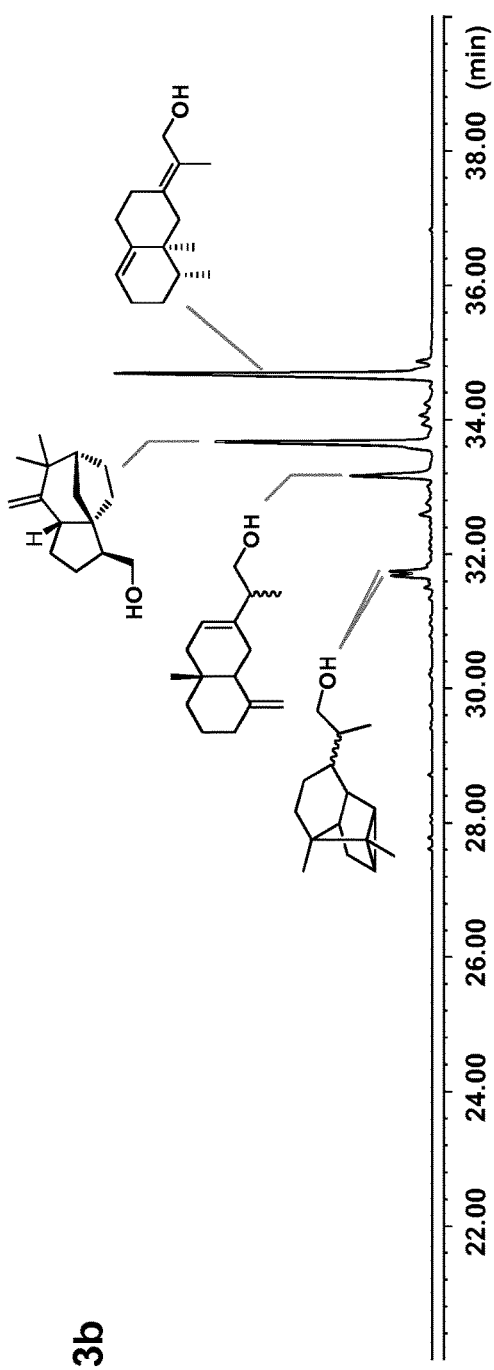

The above-mentioned differences in chemical composition between the vetiveryl ester according to one or more embodiments of the present disclosure and commercial vetiveryl acetates as well as vetiveryl acetates obtained by chemical process, are also illustrated in FIG. 3a, which shows a chromatogram of an isolated ester fraction of a vetiveryl acetate according to one or more embodiments of the present disclosure, and FIG. 3b, which shows a chromatogram of the saponification products of the isolated ester fraction of FIG. 3a. In view of FIGS. 3a and 3b, it becomes apparent that the vetiveryl acetate mainly comprises esters of primary alcohol compounds such as cyclocopacamphanyl acetate A, cyclocopacamphanyl acetate B, vetiselinenyl acetate, khusimyl acetate, (E)-isovalencenyl acetate and (Z)-isovalencenyl acetate.

Figure 4A:
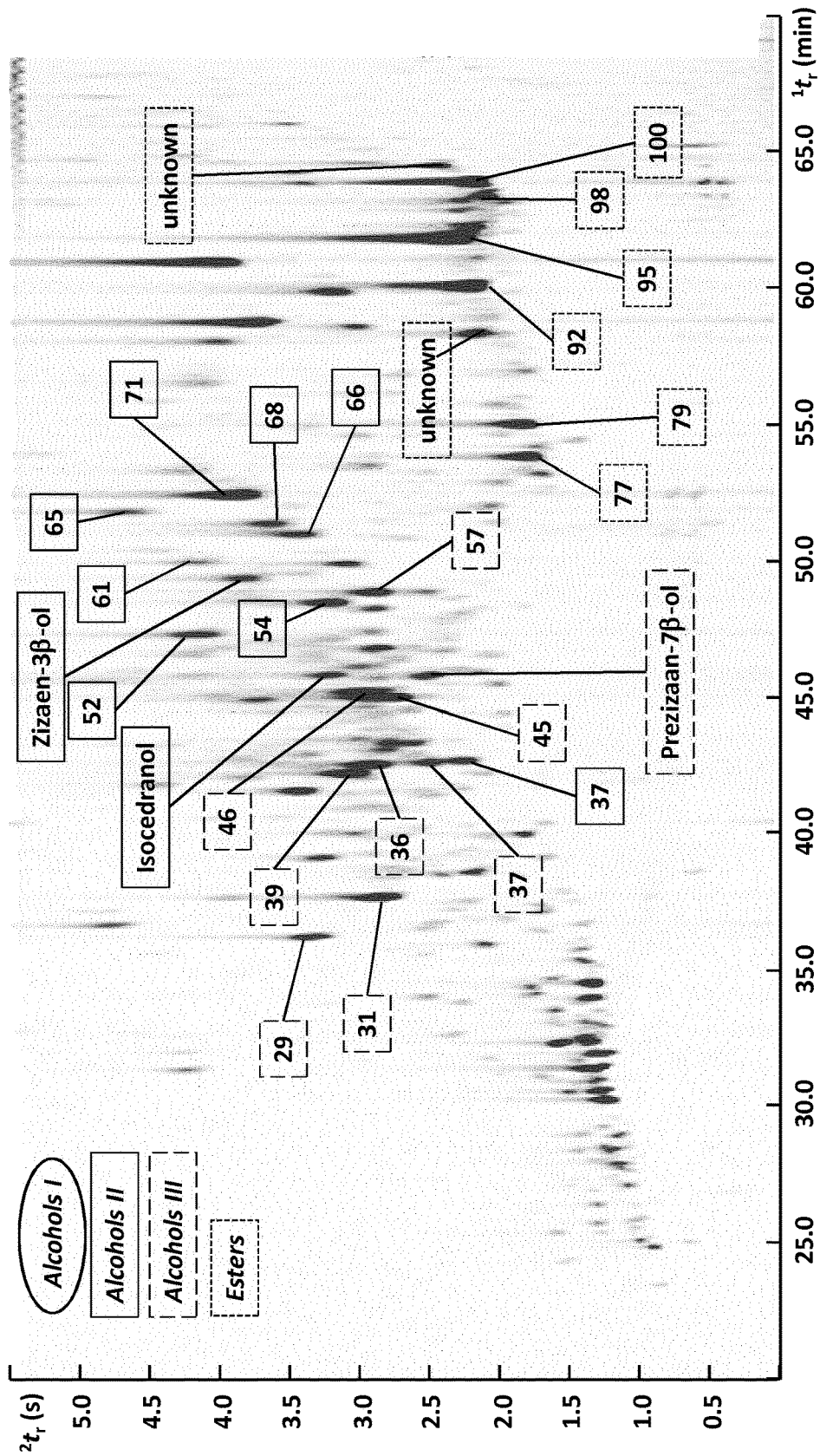
FIGS. 4a to 4d show comprehensive two-dimensional gas chromatography-mass spectrometry chromatogram of a vetiveryl ester according to one or more embodiments of the present disclosure, Haitian vetiver essential oil, a commercial vetiveryl acetate, and a vetiveryl acetate obtained by chemical process, respectively.
Figure 4B:
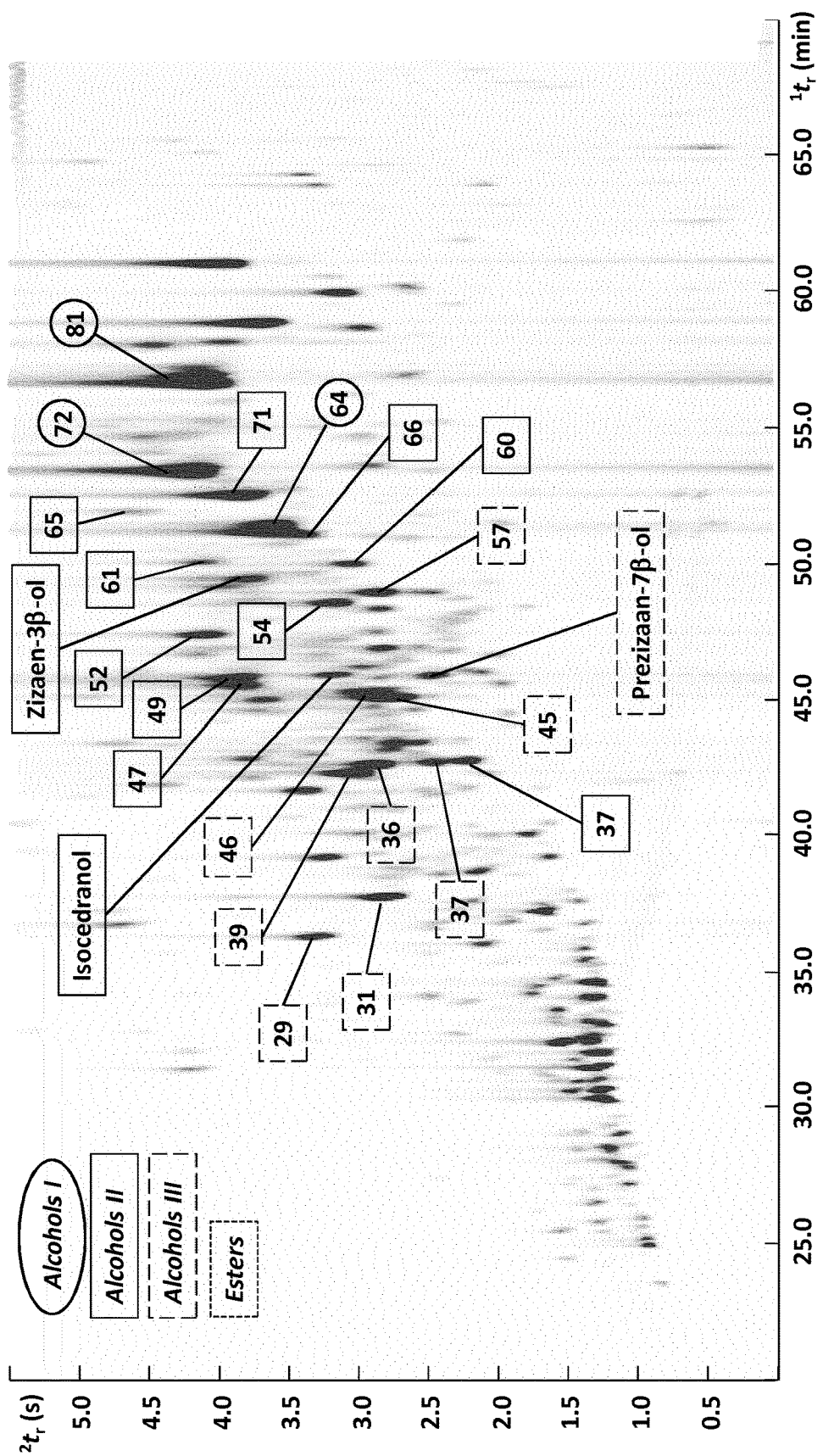
Figure 4C:
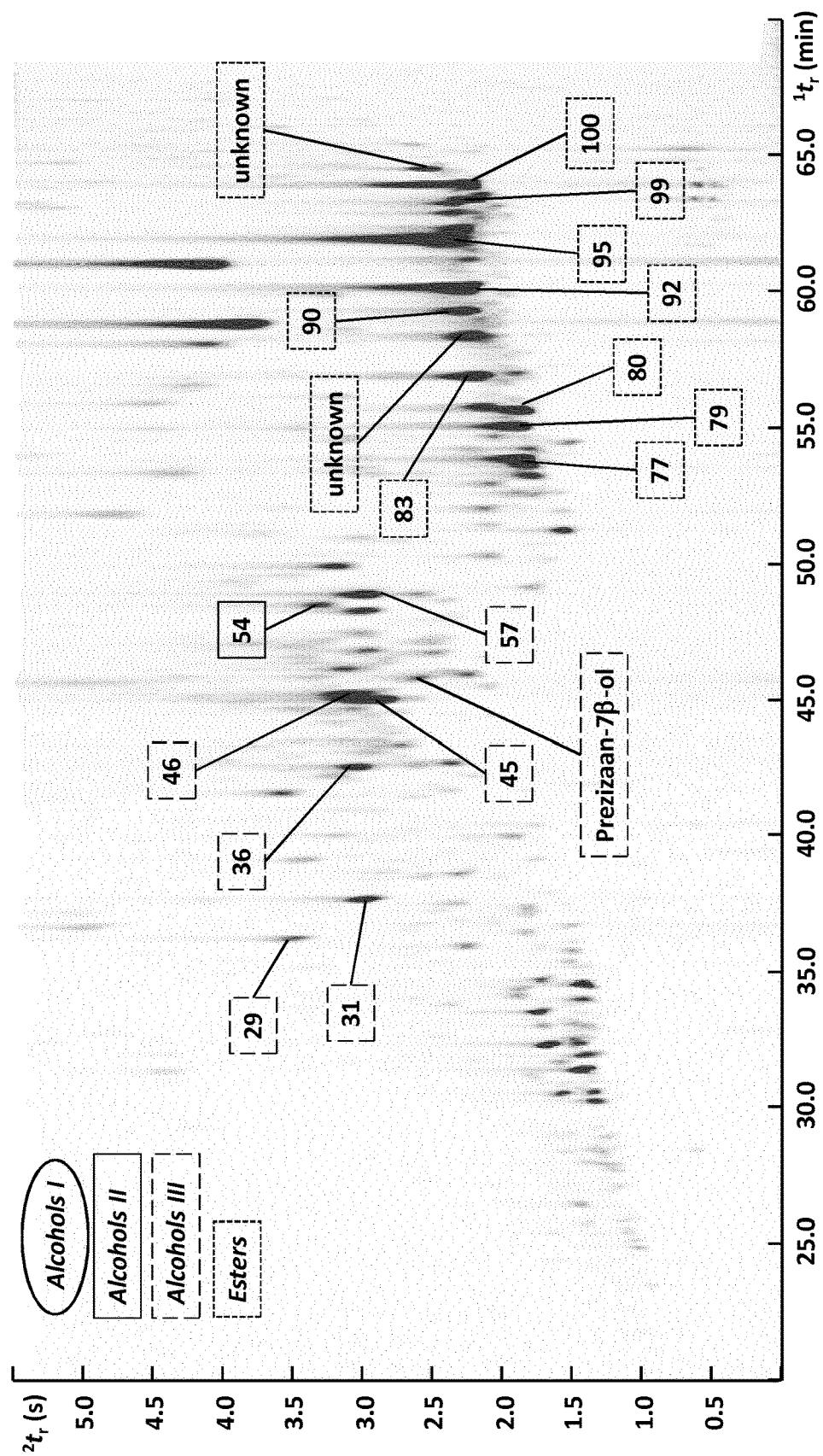
Figure 4D:
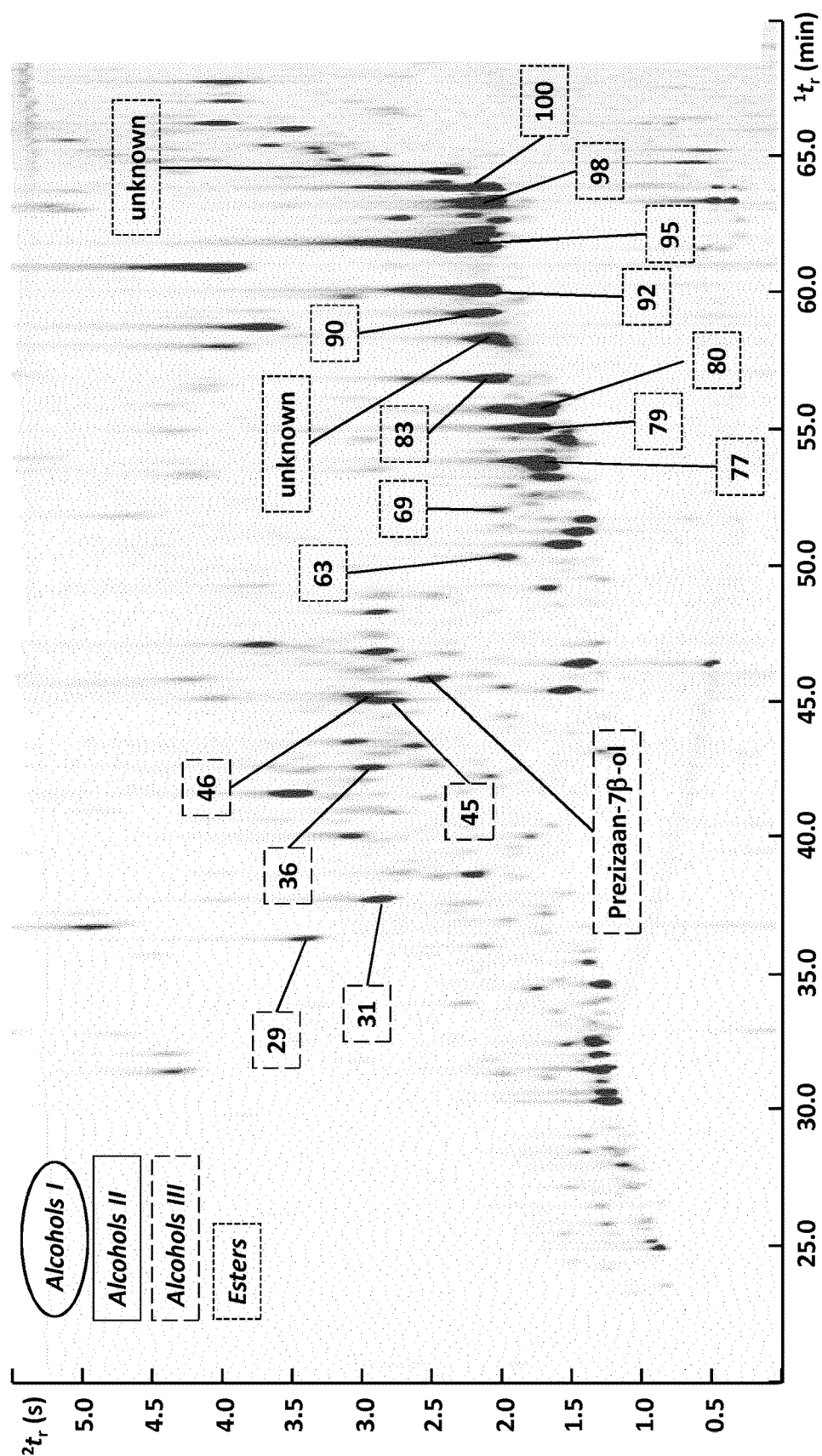

The above-mentioned differences in chemical composition between the vetiveryl ester according to one or more embodiments of the present disclosure, Haitian vetiver essential oil, commercial vetiveryl acetates and vetiveryl acetates obtained by chemical process, are also illustrated in FIGS. 4a to 4d, which show respective comprehensive two-dimensional GC-MS chromatograms. It becomes apparent from FIG. 4a compared to FIG. 4b, that substantially all primary alcohol compounds present in the vetiver oil are esterified (e.g. no more than 5 weight percent); that the vetiveryl acetate according to one or more embodiments of the present disclosure comprises a great amount of secondary alcohol compounds, which have not been esterified by the process according to present disclosure (e.g. at least 0.5 weight percent); and that said vetiveryl acetate comprises substantially the same amount of tertiary alcohol compounds as the amount of tertiary alcohol compounds present in the vetiver oil (e.g. ±5 weight percent of tertiary alcohol compounds with respect to the amount of tertiary alcohol compounds present in the vetiver oil). It becomes also apparent from FIG. 4a compared to FIGS. 4c and 4d, that the vetiveryl acetate according to one or more embodiments of the present disclosure comprises a greater amount of secondary alcohol compounds (e.g. at least 0.5 weight percent) and tertiary alcohol compounds (e.g. at least 2.5 weight percent) compared to commercial vetiveryl acetates (FIG. 4c) and vetiveryl acetates obtained by chemical process (FIG. 4d). Comprehensive two-dimensional GC-MS chromatography being highly reliable and accurate determination system, additional secondary and tertiary alcohol compounds, such as isocedranol, zizaen-3β-ol and prezizaan-7β-ol, may be identified.

As the result of the above-mentioned differences, the vetiveryl esters according to one or more embodiments of the present disclosure have an enhanced, equilibrated, long lasting, stable and pleasant set of odor notes. For example, a unique combination of olfactory notes and intensities was determined for vetiveryl acetate according to one or more embodiments of the present disclosure upon olfactory evaluation by trained perfumers. Specifically, strip samples of vetiveryl acetate (1.4 percent in ethanol) and commercial vetiveryl acetate from the target market were tested, and it was found that vetiveryl acetate according to one or more embodiments of the present disclosure had unmatched odor notes, which may be best described as follow: "The top note is a little less powerful but more balanced, the woody note is very present, the sparkling grapefruit-like effect is very good, the cedarwood-like note has smoky and then sandalwood-like undertones, the powdery-like note is present, and the heart note is well balanced". Conversely, the commercial product was found to be very smoky and cedarwood-like, less sandalwood-like, and with lower grapefruit-like and powdery-like facets.

Process for the Preparation of Vetiveryl Ester:

Vetiver oil was dissolved in food grade ethyl acetate containing 10 g/L of molecular sieve (3 Å) to provide a mixture having concentration of 10 g/L of vetiver oil. *Candida antartica* lipase adsorbed on an acrylic resin (activity 5000 U/g) was introduced in the mixture with an amount of 30 weight percent with respect to the total weight of the vetiver oil. The mixture was stirred at room temperature using an orbital shaker at 250 rpm for 5 hours. The mixture was filtered through a cotton pad. The solvent was removed at conditions of 35° C. and 150 mbar to obtain quantitatively vetiveryl acetate. The supported enzyme was recovered, washed with acetone, dried under reduced pressure and stored at low temperature (typically below 0° C.).

Quantitative and Qualitative Analytical Methods:

Chemical composition of vetiveryl esters may be determined by qualitative and/or quantitative chromatography techniques, such as a technique selected from the group comprising one-dimensional or two-dimensional liquid and gas chromatography, for example gas chromatography coupled with mass spectrometry (GC-MS), gas chromatography with flame ionisation detector (GC-FID), gas chromatography with thermal conductivity detector (GC-TCD), or comprehensive two-dimensional gas chromatography with mass spectrometry and flame ionisation detector (GC×GC-FID/MS). As illustrated in Tables 1a-h showing a vetiveryl acetate according to one or more embodiments of the present disclosure comprising about 100 compounds or more, which may coelute depending on the selected analytical conditions, the chemical composition of vetiveryl esters may be determined by comprehensive two-dimensional gas chromatography such as GC×GC-FID/MS, which is a technique of choice to accurately and reliably determine the chemical composition of vetiveryl esters.

In addition, target constituents of vetiveryl esters may be estimated by GC-MS, as shown in Tables 1a-h, where retention indexes were determined by comparison with a series of linear alkanes. Main cases of coelution were identified by GC×GC-MS and are given in the Table. For example, in one or more embodiments, response factors of compounds, such as khusimol in vetiver oil and khusimyl acetate in vetiveryl acetate, were determined using tridecane as internal reference. Authentic khusimol sample was obtained by $LiAlH_4$ reduction of zizanoic acid extracted from the oil as previously described by inventors of the present disclosure in *Chem. Biodiversity* 2014, 11, (11), 1821-1842. Khusimyl acetate was obtained by acetylation of khusimol using a standard acetylation procedure. The purity of reference compounds (over 97 percent) was controlled by GC and NMR analysis prior to use in calibration experiments.

For quantification purposes, GC analyses were carried out using an Agilent 6890N gas chromatograph equipped with a Chrompack VF1-MS capillary column (30 m×0.25 mm; 0.25 µm film thickness) and mounted with a flame ionisation detector. Analyses were run out using a 1:10 split ratio using hydrogen as carrier gas with a constant 0.8 mL/min flow. The GC oven was program as follows: 100° C. (held isothermal 5 min) increased to 250° C. at 5° C./min.

1D-GC-MS analyses were performed using an Agilent 6890N/5973N GC-MS system mounted with a J&W HP-1MS (60 m×0.25 mm; 0.2 µm film thickness). Column flow (He) 1.0 mL/min; Split ratio 1/100; temperature program: 100° C. (held 5 min isothermal) increased to 250° C. at 5° C./min (4.5 min final isotherm). The mass spectrometer was operated at 70 eV over a 35-350 m/z range. Essential oil constituents were identified upon cross-correlation of their retention indices calculated from a series of n-alkanes, and their mass spectra matched against commercial libraries (Wiley275, NIST08) or in-house MS databases built from literature information, and isolated or synthesized substances.

Comprehensive two-dimensional gas chromatography-mass spectrometry (GC×GC-MS) was performed using an Agilent 6890N/5973N GC-MS system equipped with a cryogenic GC×GC ZOEX kit. The two-dimensional GC column set was composed of a Chrompack VF-5MS (30 m×0.25 mm; 0.2 µm film thickness) and a J&W DB-Wax (1.25 m×0.10 mm; 0.1 µm film thickness) coupled through a deactivated fused silica capillary tube (1.25 m×0.10 mm) installed as a loop in the cryogenic modulator. Column flow (He) 0.7 mL/min; Split ratio 1/100; Main oven temperature program: 50° C. to 140° C. by 10° C./min, 140° C. to 188° C. at 1° C./min, 188° C. to 200° C. by 2° C./min, then 200° C. to 250° C. by 20° C. min (4.5 min final isotherm.). Secondary Oven temperature program: 50° C. to 140° C. by 10° C./min, 140° C. to 150° C. by 1.25° C./min, 150° C. to 250° C. by 3° C./min. Modulation period, $P_M$: 5.5 s. The Mass spectrometer was operated at 70 eV in fast scan mode over a 50-280 amu range corresponding to a 24.67 Hz acquisition rate. Essential oil constituents were identified upon cross-correlation of their retention indices calculated from a series of n-alkanes, and their mass spectra matched against commercial libraries (Wiley275, NIST08) or in-house MS databases built from literature information, and isolated or synthesized substances.

Additional exemplary chemical composition determination techniques applicable to vetiveryl esters are described by Inventors of the present disclosure in the experimental part of *J. Chromatogr. A* 2013, 1288, 127-148.

Although the above-mentioned embodiments have been described in detail, it is understood that alternative embodiments of the disclosure may be envisaged. So for example, in one or more embodiments, the process is performed with an enzyme preparation other than *Candida antartica* lipase and/or a non supported enzyme preparation. Also, in one or more embodiments, the acylating compound is a compound other than ethyl acetate. Also, in one or more embodiments, the presence of a drying agent such as molecular sieve (3 Å) is not required. In the same manner, analytic methods other than 1-D and/or 2-D liquid and gas chromatography may be used to identify the vetiveryl esters composition.

TABLE 1a

| Peak # | $T_r$ (min) | Prog. RI (HP1) | Compound name | Chemical class |
|---|---|---|---|---|
| 1 | 20.500 | 1350 | 91 105 (117) 119 132 145 173 188 | Unknown H. |
| 2 | 20.606 | 1352 | α-Cubebene | Hydrocarbons |
| 3 | 21.410 | 1370 | Dehydronigritene | Hydrocarbons |
| 4 | 21.622 | 1375 | α-Ylangene | Hydrocarbons |
| 5 | 21.723 | 1377 | Cyclosativene | Hydrocarbons |
| 6 | 22.087 | 1385 | trans-2-nor-Zizaene (HCA 1983 828) | Hydrocarbons |
| 7 | 22.479 | 1394 | β-Elemene | Hydrocarbons |
| 8 | 23.279 | 1409 | α-Funebrene | Hydrocarbons |
| 9 | 23.637 | 1415 | Acora-3,7(14)-diene | Hydrocarbons |
| 11 | 23.892 | 1419 | Cascarilladiene | Hydrocarbons |
| 10 | 24.068 | 1422 | β-Funebrene | Hydrocarbons |
| 12 | 24.673 | 1433 | β-Copaene | Hydrocarbons |
| 13 | 25.208 | 1442 | Guai-6,9-diene | Hydrocarbons |
| 14 | 25.701 | 1450 | Prezizaene | Hydrocarbons |
| 15 | 26.003 | 1455 | Zizaene + Selina-4(15),7-diene | Hydrocarbons |
| 16 | 26.631 | 1466 | Spirovetiva-1(10),2,7(11)-triene | Hydrocarbons |
| 17 | 26.856 | 1470 | (145) 159 187 202 | Unknown H. |
| 18 | 27.375 | 1479 | α-Amorphene | Hydrocarbons |
| 19 | 27.723 | 1485 | cis-Eudesma-6,11-diene (+α-vetispirene)* | Hydrocarbons |
| 20 | 28.002 | 1489 | β-Vetispirene | Hydrocarbons |
| 21 | 28.205 | 1493 | γ-Amorphene | Hydrocarbons |
| 22 | 29.002 | 1505 | δ-Amorphene + Eremophila-1(10),2,7(11)-triene | Hydrocarbons |
| 23 | 29.430 | 1511 | cis/trans-Calamenene | Hydrocarbons |
| 24 | 29.686 | 1515 | Spirovetiva-1(10),7(11)-diene | Hydrocarbons |
| 25 | 29.844 | 1517 | δ-Cadinene (+Spirovetiva-1(10),7(11)-diene)* | Hydrocarbons |
| 26 | 30.072 | 1520 | Eremophila-1(10),7(11)-diene | Hydrocarbons |

TABLE 1b

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 1 | 0.941 | 0.018 | 0.000 | — | — | — | — | — | — |
| 2 | 0.959 | 0.020 | 0.000 | — | — | — | — | — | — |
| 3 | 0.941 | 0.064 | 0.005 | — | — | 0.037 | 0.000 | 0.047 | 0.000 |
| 4 | 0.959 | 0.061 | 0.002 | — | — | 0.033 | 0.000 | 0.045 | 0.000 |
| 5 | 0.959 | 0.121 | 0.003 | 0.034 | 0.001 | 0.110 | 0.001 | 0.093 | 0.000 |
| 6 | 0.954 | 0.026 | 0.001 | — | — | 0.017 | 0.000 | 0.019 | 0.001 |
| 7 | 0.959 | 0.087 | 0.001 | — | — | 0.077 | 0.000 | 0.072 | 0.000 |
| 8 | 0.959 | — | — | — | — | 0.032 | 0.000 | 0.039 | 0.000 |
| 9 | 0.959 | 0.099 | 0.001 | 0.013 | 0.010 | 0.077 | 0.001 | 0.082 | 0.001 |
| 11 | 0.959 | 0.070 | 0.001 | 0.032 | 0.002 | 0.121 | 0.001 | 0.145 | 0.001 |
| 10 | 0.959 | 0.178 | 0.001 | — | — | 0.041 | 0.001 | 0.050 | 0.002 |
| 12 | 0.959 | 0.161 | 0.000 | 0.044 | 0.000 | 0.119 | 0.005 | 0.137 | 0.003 |
| 13 | 0.959 | 0.128 | 0.000 | — | — | 0.099 | 0.005 | 0.110 | 0.003 |
| 14 | 0.959 | 0.372 | 0.001 | 0.092 | 0.000 | 0.281 | 0.011 | 0.314 | 0.012 |
| 15 | 0.959 | 0.761 | 0.001 | 0.175 | 0.000 | 0.555 | 0.019 | 0.646 | 0.026 |
| 16 | 0.947 | 0.184 | 0.004 | 0.122 | 0.001 | 0.128 | 0.017 | 0.155 | 0.019 |
| 17 | 0.947 | 0.196 | 0.003 | — | — | — | — | — | — |
| 18 | 0.959 | 1.350 | 0.006 | 0.482 | 0.012 | 1.151 | 0.021 | 1.199 | 0.033 |

TABLE 1b-continued

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 19 | 0.959 | 0.376 | 0.005 | 0.214 | 0.004 | 0.424 | 0.017 | 0.341 | 0.016 |
| 20 | 0.947 | 1.127 | 0.012 | 0.445 | 0.005 | 0.864 | 0.014 | 0.948 | 0.012 |
| 21 | 0.959 | 0.472 | 0.002 | 0.195 | 0.005 | 0.392 | 0.014 | 0.428 | 0.014 |
| 22 | 0.959 | 0.618 | 0.021 | 0.366 | 0.013 | 0.753 | 0.023 | 0.436 | 0.013 |
| 23 | 1.019 | 0.182 | 0.002 | 0.093 | 0.004 | 0.114 | 0.014 | 0.186 | 0.008 |
| 24 | 0.959 | — | — | 0.170 | 0.006 | 0.216 | 0.012 | 0.267 | 0.009 |
| 25 | 0.959 | 0.262 | 0.003 | 0.110 | 0.003 | 0.218 | 0.009 | 0.247 | 0.006 |
| 26 | 0.959 | 0.928 | 0.004 | 0.467 | 0.008 | 0.798 | 0.022 | 0.834 | 0.008 |

TABLE 1c

| Peak # | $T_r$ (min) | Prog. RI (HP1) | Compound name | Chemical class |
|---|---|---|---|---|
| 27 | 30.340 | 1524 | γ-Vetivenene | Hydrocarbons |
| 28 | 30.883 | 1532 | α-Calacorene | Hydrocarbons |
| 29 | 31.276 | 1537 | β-Elemol | Alcohols III |
| 30 | 32.010 | 1548 | β-Vetivenene | Hydrocarbons |
| 31 | 32.358 | 1553 | cis-Eudesm-6-en-11-ol | Alcohols III |
| 32 | 33.131 | 1564 | 109 137 (152) 222 | Unknown |
| 33 | 33.518 | 1569 | (59) 91 205 220 | Unknown |
| 34 | 34.217 | 1579 | Khusimone (+unknown 187 202)* | Ketones |
| 35 | 34.433 | 1582 | 119 147 (162) 204 | |
| 36 | 36.197 | 1606 | Eudesm-6-en-4-ol (epimer A) | Alcohols III |
| 37 | 36.413 | 1609 | Junenol | Alcohols II |
| 38 | 36.433 | 1609 | 10-epi-γ-Eudesmol | Alcohols III |
| 39 | 36.498 | 1610 | Eudesm-6-en-4-ol (epimer B) + Junenol* | Alcohols III |
| 40 | 36.940 | 1616 | β-Eudesmol + unknown 145 218* | Alcohols III |
| 41 | 37.019 | 1617 | 13-nor-Eremophila-1(10),6-dien-11-one | Ketones |
| 42 | 37.308 | 1620 | 1-epi-Cubenol | Alcohols III |
| 43 | 37.568 | 1624 | α-Funebren-15-al | Aldehydes |
| 44 | 38.477 | 1635 | 7-epi-α-Eudesmol | Alcohols III |
| 45 | 38.791 | 1639 | α-Cadinol + Valerianol | Alcohols III |
| 46 | 39.072 | 1643 | α-Eudesmol | Alcohols III |
| 47 | 39.094 | 1643 | Cyclocopacamphanol A | Alcohols I |
| 48 | 39.209 | 1644 | Ziza-6(13)-en-3-one (+coelution) | Ketones |
| 49 | 39.299 | 1646 | Cyclocopacamphanol B | Alcohols I |
| 50 | 39.556 | 1649 | 91 107 121 145 187 (202) | Unknown OH |
| 51 | 39.786 | 1652 | Isocedranol | Alcohols II |
| 52 | 40.109 | 1656 | Ziza-6(13)-en-3a-ol (+2-epi-Ziza-6(13)-en-3-one)* | Alcohols II |

TABLE 1d

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 27 | 1.019 | — | — | 0.227 | 0.020 | 0.253 | 0.023 | 0.297 | 0.022 |
| 28 | 1.008 | 0.306 | 0.002 | 0.180 | 0.004 | 0.286 | 0.014 | 0.303 | 0.009 |
| 29 | 0.879 | 0.698 | 0.003 | 0.331 | 0.010 | 0.263 | 0.007 | 0.641 | 0.010 |
| 30 | 0.947 | 0.921 | 0.038 | 0.116 | 0.021 | 0.749 | 0.008 | 0.564 | 0.011 |
| 31 | 0.879 | 1.638 | 0.005 | 0.621 | 0.031 | 0.232 | 0.005 | 1.524 | 0.020 |
| 32 | 0.879 | 0.469 | 0.010 | — | — | 0.384 | 0.009 | 0.393 | 0.010 |
| 33 | 0.868 | 0.699 | 0.005 | — | — | — | — | 0.637 | 0.022 |
| 34 | 0.865 | 1.141 | 0.010 | 0.381 | 0.037 | 0.942 | 0.007 | 0.955 | 0.017 |
| 35 | 0.865 | 0.204 | 0.001 | — | — | 0.158 | 0.004 | — | — |
| 36 | 0.879 | 1.773 | 0.002 | 0.663 | 0.054 | 0.925 | 0.005 | 1.515 | 0.027 |
| 37 | 0.879 | — | — | 0.455 | 0.035 | — | — | — | — |
| 38 | 0.879 | — | — | — | — | 0.337 | 0.008 | — | — |
| 39 | 0.879 | 3.162 | 0.005 | — | — | — | — | 2.748 | 0.031 |
| 40 | 0.879 | — | — | 0.168 | 0.058 | — | — | 0.730 | 0.014 |

TABLE 1d-continued

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 41 | 0.865 | — | — | — | — | 0.146 | 0.029 | — | — |
| 42 | 0.879 | 0.739 | 0.001 | 0.339 | 0.048 | 0.449 | 0.006 | 0.666 | 0.021 |
| 43 | 0.856 | 0.465 | 0.000 | — | — | 0.230 | 0.006 | — | — |
| 44 | 0.879 | — | — | 0.556 | 0.007 | — | — | 1.225 | 0.036 |
| 45 | 0.868 | 3.349 | 0.005 | 2.869 | 0.039 | 1.140 | 0.016 | 2.980 | 0.044 |
| 46 | 0.879 | — | — | 0.290 | 0.009 | — | — | 0.375 | 0.014 |
| 47 | 0.868 | 1.551 | 0.009 | — | — | — | — | — | — |
| 48 | 0.856 | — | — | — | — | 0.745 | 0.010 | 0.786 | 0.044 |
| 49 | 0.868 | 2.464 | 0.014 | — | — | — | — | — | — |
| 50 | 0.868 | — | — | — | — | — | — | 0.298 | 0.009 |
| 51 | 0.879 | 0.559 | 0.001 | — | — | — | — | 0.473 | 0.021 |
| 52 | 0.868 | 1.888 | 0.003 | — | — | — | — | 1.657 | 0.048 |

TABLE 1e

| Peak # | $T_r$ (min) | Prog. RI (HP1) | Compound name | Chemical class |
|---|---|---|---|---|
| 53 | 40.255 | 1658 | 2-epi-Ziza-6(13)-en-3-one | Ketones |
| 54 | 40.678 | 1663 | Khusian-2-ol | Alcohols II |
| 55 | 40.680 | 1663 | β-Elemol acetate (tent. MS) | unknown ester |
| 56 | 40.985 | 1667 | cis-Eudesm-6-en-11-ol, acetate (tent. MS) | unknown ester |
| 57 | 41.865 | 1678 | Juniper Camphor | Alcohols III |
| 58 | 41.875 | 1678 | Juniper Camphor (+Ziza-6(13)-en-3β-ol)* | Alcohols III |
| 59 | 42.121 | 1681 | (E)-Opposita-4(15),7,11-dien-12-al | Aldehydes |
| 60 | 42.867 | 1691 | 13-nor-Eudesma-4,6-dien-11-one | Ketones |
| 61 | 43.269 | 1696 | Nootkatol | Alcohols II |
| 62 | 43.500 | 1698 | 1,7-Cyclogermacra-1(10),4-dien-15-al | Aldehydes |
| 63 | 43.558 | 1699 | 12-nor-Ziza-6(13)-en-2β-yl acetate | Esters |
| 64 | 44.002 | 1705 | Vetiselinenol | Alcohols I |
| 65 | 44.390 | 1709 | Oplopanone | Ketones |
| 66 | 44.409 | 1710 | β-Isonootkatol | Alcohols II |
| 67 | 44.736 | 1713 | Isocedranol acetate (tent. MS) | Unknown ester |
| 68 | 44.925 | 1716 | β-Vetivol | Alcohols II |
| 69 | 45.072 | 1718 | 12-nor-Ziza-6(13)-en-2α-yl acetate | Esters |
| 70 | 45.552 | 1723 | 10-epi-γ-Eudesmol, acetate (tent. MS) | Unknown ester |
| 71 | 45.538 | 1723 | Isonootkatol | Alcohols II |
| 72 | 45.556 | 1723 | Khusimol (+α-isonootkatol)* | Alcohols I |
| 73 | 45.765 | 1726 | Amorphenyl ester (tent. MS) | Unknown ester |
| 74 | 46.673 | 1737 | Cadinyl ester (tent. MS) | Unknown ester |
| 75 | 46.844 | 1739 | unknown ester (159)264 | Unknown ester |
| 76 | 47.095 | 1742 | unknown ester (159) 264 | Unknown ester |
| 77 | 47.359 | 1745 | Cyclocopacamphanyl acetate A | Esters |
| 78 | 47.589 | 1748 | Valencen-12-ol | Alcohols I |

TABLE 1f

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 53 | 0.856 | — | — | 0.903 | 0.032 | 0.809 | 0.009 | — | — |
| 54 | 0.879 | 1.561 | 0.003 | 0.679 | 0.034 | — | — | 1.291 | 0.038 |
| 55 | 0.814 | — | — | — | — | 0.734 | 0.005 | — | — |
| 56 | 0.814 | — | — | — | — | 1.297 | 0.004 | — | — |
| 57 | 0.879 | — | — | 1.149 | 0.023 | 0.643 | 0.004 | 1.285 | 0.035 |
| 58 | 0.879 | 2.164 | 0.006 | — | — | — | — | — | — |
| 59 | 0.856 | 0.471 | 0.001 | — | — | 0.242 | 0.003 | — | — |
| 60 | 0.844 | 0.756 | 0.001 | 0.728 | 0.020 | 1.038 | 0.003 | 0.611 | 0.032 |
| 61 | 0.868 | 0.905 | 0.003 | — | — | — | — | 0.288 | 0.031 |
| 62 | 0.856 | — | — | — | — | — | — | 0.192 | 0.036 |

TABLE 1f-continued

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 63 | 0.791 | — | — | 0.286 | 0.024 | 0.400 | 0.005 | — | — |
| 64 | 0.868 | 3.686 | 0.010 | — | — | — | — | 0.424 | 0.039 |
| 65 | 0.800 | — | — | 0.538 | 0.031 | — | — | 1.080 | 0.054 |
| 66 | 0.868 | 1.158 | 0.006 | — | — | — | — | — | — |
| 67 | 0.814 | — | — | — | — | 0.777 | 0.005 | — | — |
| 68 | 0.868 | 0.648 | 0.014 | — | — | — | — | 1.067 | 0.055 |
| 69 | 0.791 | — | — | 0.226 | 0.017 | 0.210 | 0.004 | — | — |
| 70 | 0.814 | — | — | — | — | 0.981 | 0.007 | — | — |
| 71 | 0.868 | — | — | — | — | — | — | 3.243 | 0.063 |
| 72 | 0.868 | 13.445 | 0.014 | 0.419 | 0.019 | — | — | — | — |
| 73 | 0.814 | — | — | — | — | 0.823 | 0.006 | — | — |
| 74 | 0.814 | — | — | — | — | 0.899 | 0.015 | — | — |
| 75 | 0.814 | — | — | 0.722 | 0.088 | — | — | 0.410 | 0.026 |
| 76 | 0.814 | — | — | 0.718 | 0.013 | — | — | — | — |
| 77 | 0.804 | — | — | 2.321 | 0.022 | 1.613 | 0.005 | 1.121 | 0.035 |
| 78 | 0.868 | 0.516 | 0.004 | — | — | — | — | — | — |

TABLE 1g

| Peak # | $T_r$ (min) | Prog. RI (HP1) | Compound name | Chemical class |
|---|---|---|---|---|
| 79 | 48.526 | 1759 | Cyclocopacamphanyl acetate B | Esters |
| 80 | 48.718 | 1761 | Khusian-2-yl acetate | Esters |
| 81 | 49.438 | 1770 | (E)-Isovalencenol | Alcohols I |
| 82 | 49.726 | 1773 | Nootkatone | Ketones |
| 83 | 49.866 | 1775 | Ziza-6(13)-en-3α-yl acetate | Esters |
| 84 | 50.007 | 1777 | Spirovetiva-3,7(11)-dien-12-ol | Alcohols I |
| 85 | 50.324 | 1781 | unknown alcohol I (187 202) 220 | Alcohols I |
| 86 | 50.875 | 1787 | β-Vetivone | Ketones |
| 87 | 51.137 | 1790 | Zizanoic acid | Acids |
| 88 | 51.280 | 1792 | unknown ester 159 | Unknown ester |
| 89 | 51.925 | 1800 | (E)-Isovalencenal | Aldehydes |
| 90 | 52.163 | 1803 | Ziza-6(13)-en-3β-yl acetate | Esters |
| 91 | 52.657 | 1808 | α-Vetivone | Ketones |
| 92 | 53.406 | 1817 | Vetiselinenyl acetate | Esters |
| 93 | 53.821 | 1822 | Spirovetivadienal A | Aldehydes |
| 94 | 54.274 | 1827 | Spirovetivadienal B | Aldehydes |
| 95 | 54.935 | 1835 | Khusimyl acetate | Esters |
| 96 | 55.883 | 1846 | unknown ester | Unknown ester |
| 97 | 56.65 | 1855 | Spirovetivadien-2-yl acetate | Esters |
| 98 | 57.533 | 1865 | (Z)-Isovalencenyl acetate | Esters |
| 99 | 57.704 | 1867 | Isonootkatyl acetate | Esters |
| 100 | 58.617 | 1878 | (E)-Isovalencenyl acetate (+spirovetivadien-12-yl acetate)* | Esters |
| 101 | 58.913 | 1881 | unknown ester 262 | Unknown ester |
| 102 | 59.443 | 1888 | unknown ester (187 202) 262 | Unknown ester |

TABLE 1h

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 79 | 0.804 | — | — | 2.305 | 0.031 | 1.480 | 0.002 | 1.431 | 0.054 |
| 80 | 0.814 | — | — | 1.944 | 0.015 | 2.279 | 0.017 | — | — |
| 81 | 0.868 | 11.396 | 0.018 | — | — | — | — | 1.022 | 0.048 |
| 82 | 0.856 | 0.925 | 0.006 | 0.980 | 0.026 | 0.757 | 0.003 | 0.693 | 0.030 |
| 83 | 0.804 | — | — | 2.011 | 0.008 | 1.235 | 0.005 | — | — |
| 84 | 0.868 | 2.072 | 0.004 | — | — | — | — | — | — |
| 85 | 0.868 | 1.118 | 0.002 | — | — | — | — | — | — |
| 86 | 0.856 | 4.320 | 0.038 | 5.828 | 0.053 | 3.988 | 0.014 | 4.275 | 0.071 |

TABLE 1h-continued

| | | Haiti Vetiver Essential Oil | | Commercial vetiveryl acetate | | Chemical vetiveryl acetate Ex. Haiti | | Enzymatic vetiveryl acetate Ex. Haiti | |
|---|---|---|---|---|---|---|---|---|---|
| Peak # | RRF | g/100 g | St.D/3 | g/100 g | St.D/3 | g/100 g | St.D/3 | g/100 g | St.D/3 |
| 87 | 0.777 | 0.750 | 0.035 | — | — | — | — | 0.585 | 0.011 |
| 88 | 0.804 | | | | | | | 0.497 | 0.027 |
| 89 | 0.856 | 0.933 | 0.003 | — | — | 0.991 | 0.005 | 1.013 | 0.039 |
| 90 | 0.804 | — | — | 1.197 | 0.013 | 0.702 | 0.004 | — | — |
| 91 | 0.856 | 4.868 | 0.007 | 6.016 | 0.058 | 4.484 | 0.006 | 4.722 | 0.070 |
| 92 | 0.804 | — | — | 7.562 | 0.069 | 4.538 | 0.008 | 3.726 | 0.059 |
| 93 | 0.856 | 0.037 | 0.005 | — | — | — | — | — | — |
| 94 | 0.856 | 0.090 | 0.002 | — | — | — | — | — | — |
| 95 | 0.804 | — | — | 20.410 | 0.193 | 10.331 | 0.009 | 9.950 | 0.086 |
| 96 | 0.804 | | | — | — | | | 0.821 | 0.023 |
| 97 | 0.804 | — | — | 0.650 | 0.013 | 1.297 | 0.004 | 0.483 | 0.015 |
| 98 | 0.804 | — | — | 0.399 | 0.014 | — | — | 1.174 | 0.018 |
| 99 | 0.804 | — | — | 1.057 | 0.007 | 4.186 | 0.010 | — | — |
| 100 | 0.804 | — | — | 14.878 | 0.166 | 14.530 | 0.022 | 14.059 | 0.118 |
| 101 | 0.804 | — | — | 0.303 | 0.059 | 0.507 | 0.001 | 0.514 | 0.007 |
| 102 | 0.804 | — | — | 0.616 | 0.004 | 0.673 | 0.002 | 0.601 | 0.006 |

*coelution

The invention claimed is:

1. A vetiveryl ester composition comprising at least 0.5 weight percent of secondary alcohol compounds with respect to the total weight of the vetiveryl ester composition.

2. A vetiveryl ester composition according to claim 1, wherein the secondary alcohol compounds comprise at least one alcohol selected from the group comprising 12-nor-zizaen-2β-ol, junenol, ziza-6(13)-en-3α-ol, khusian-2-ol, nootkatol, β-vetivol, β-isonootkatol and α-isonootkatol.

3. A vetiveryl ester composition according to claim 1, comprising no more than 5 weight percent of primary alcohol compounds with respect to the total weight of the vetiveryl ester.

4. A vetiveryl ester composition according to claim 3, wherein the primary alcohol compounds comprise at least one alcohol selected from the group comprising: cyclocopacamphanol A, cyclocopacamphanol B, vetiselinenol, khusimol, valencen-12-ol, (H)-isovalencenol and spirovetivadien-12-ol.

5. A vetiveryl ester composition according to claim 1, comprising at least 2.5 weight percent of tertiary alcohol compounds with respect to the total weight of the vetiveryl ester.

6. A vetiveryl ester composition according to claim 5, wherein the tertiary alcohol compounds comprise at least one alcohol selected from the group comprising: elemol, cis-eudesm-6-en-11-ol, cis-eudesm-6-en-4-ol A, cis-eudesm-6-en-4-ol B, 10-epi-γ-eudesmol, β-eudesmol, 1-epi-cubenol, hinesol, α-cadinol epimer, α-cadinol, valerianol, α-eudesmol, intermedeol and juniper camphor.

7. A vetiveryl ester composition according to claim 1, comprising from about 1 to about 50 weight percent of ester compounds with respect to the total weight of the vetiveryl ester.

8. A process for the preparation of a vetiveryl ester composition, the process comprising:
providing a vetiver oil, at least one enzyme preparation and at least one acylating compound; and
allowing sufficient time for the enzyme preparation to react with the acylating compound and with alcohol compounds of the vetiver oil and esterify the vetiver oil.

9. The process according to claim 8, wherein the esterification is performed in presence of a drying agent.

10. The process according to claim 8, wherein the enzyme preparation comprises at least one esterase, at least one lipase; and/or wherein the enzyme preparation is a supported enzyme preparation.

11. The process according to claim 8, wherein at least one acylating compound comprises at least one carboxylic acid derived functional group.

12. The process according to claim 11, wherein at least one carboxylic acid derived functional group comprises a carboxylic ester.

13. The process according to claim 12, wherein the carboxylic ester is ethyl acetate.

14. A vetiveryl ester composition obtained by the process according to claim 8.

15. A fragrance composition comprising:
the vetiveryl ester composition comprising at least 0.5 weight percent of secondary alcohol compounds with respect to the total weight of the vetiveryl ester;
wherein the vetiveryl ester composition is prepared by the process according to claim 8.

16. A vetiveryl ester composition of claim 14, comprising at least 0.5 weight percent of secondary alcohol compounds with respect to the total weight of the vetiveryl ester, wherein the vetiveryl ester is used.

* * * * *